United States Patent
Koezuka et al.

(10) Patent No.: US 7,029,671 B1
(45) Date of Patent: Apr. 18, 2006

(54) METHOD FOR ACTIVATING HUMAN ANTIGEN-PRESENTING CELLS, ACTIVATED HUMAN ANTIGEN-PRESENTING CELLS, AND USE THEREOF

(75) Inventors: Yasuhiko Koezuka, Gunma (JP); Yasunori Yamaguchi, Gunma (JP); Kazuhiro Motoki, Gunma (JP)

(73) Assignee: Kirin Brewery Company, Limited, Tokyo (JP)

( * ) Notice: Subject to any disclaimer, the term of this patent is extended or adjusted under 35 U.S.C. 154(b) by 1026 days.

(21) Appl. No.: 09/721,768

(22) Filed: Nov. 27, 2000

Related U.S. Application Data

(62) Division of application No. 09/331,789, filed as application No. PCT/JP97/04832 on Dec. 25, 1997.

(30) Foreign Application Priority Data

Dec. 27, 1996 (JP) ............................................ 8-350429

(51) Int. Cl.
*A61K 31/7008* (2006.01)
*A61K 35/28* (2006.01)
*C12N 5/10* (2006.01)

(52) U.S. Cl. .................... 424/93.7; 424/93.71; 424/577; 435/325; 435/385; 435/386; 514/24

(58) Field of Classification Search .................. 514/24; 424/93.1, 93.7, 93.71, 577; 435/325, 385, 435/386
See application file for complete search history.

(56) References Cited

FOREIGN PATENT DOCUMENTS

WO    WO 93/05055    4/1992

OTHER PUBLICATIONS

O'Doherty, U. et al "Dendritic cells freshly isolated from human blood . . . " J. Exp. Med. vol. 178, pp. 1067–1078, 1993.*

Grabbe et al., "Dendritic Cells As Initiators Of Tumor Immune Response: A Possible Strategy For Tumor Immunotherapy", Immunology Today, Elsevier Science Ltd., vol. 16(3):117–121, (1995).

M. Crowley et al., "The cell surface of mouse dendritic cells: FACS analyses of dendritic cells from different tissues including thymus[1].", Cellular Immunology, 118, pp. 108–125, 1989.

Kayo Inaba et al., "Generation of large numbers of dendritic cells from mouse bone marrow cultures supplemented with granulocyte/macrophage colony–stimulating factor.", J. Exp. Med., vol. 176, pp. 1693–1702, 1992.

Margit D. Witmer–Pack et al., "Granulocyte/macrophage colony–stimulating factor is essential for the viability and function of cultured murine epidermal langerhans cells.", J. Exp. Med., vol. 166, pp. 1484–1498, 1987.

Christina M. Celluzzi et al., "Peptide–pulsed dendritic cells induce antigen–specific, CTL–mediated protective tumor immunity.", J. Exp. Med., vol.. 183, pp. 283–287, 1996.

Paola Paglia et al., "Murine dendritic cells loaded in vitro with soluble protein prime cytotoxic T lymphocytes against tumor antigen in vivo.", J. Exp. Med., vol. 183, pp. 317–322, 1996.

Frank J. Hsu et al., "Vaccination of patients with B–cell lymphoma using autologous antigen–pulsed dendritic cells.", Nature Medicine, vol. 2, No. 1, pp. 52–58, 1996.

Frederica Sallusto et al., "Efficient presentation of soluble antigen by cultured human dendritic cells is maintained by granulocyte/macrophage colony–stimulating factor plus interleukin 4 and downregulated by tumor necrosis factor α.", J. Exp. Med., vol. 179, pp. 1109–1118, 1994.

Frances Santiago–Schwartz et al., "TNF in combination with GM–CSF enhances the differentiation of neonatal cord blood stem cells into dendritic cells and macrophages.", Journal of Leukocyte Biology, vol. 52, pp. 274–281, 1992.

C. Caux et al., "GM–CSF and TNF—α cooperate in the generatio of dendritic langerhans cells.", Nature, vol. 360, pp. 258–261, 1992.

(Continued)

*Primary Examiner*—James O. Wilson
*Assistant Examiner*—Leigh C. Maier
(74) *Attorney, Agent, or Firm*—Foley & Lardner

(57) ABSTRACT

The invention relates to a method for activating human-derived antigen-presenting cells by in vitro cultivation with at least one of the glycoside compounds represented by formula (A) or salts thereof [preferred example: (2S,3S,4R)-1-(α-D-galactopyranosyloxy)-2-hexacosanoylamino-3,4-octadecanediol], and to human antigen-presenting cells activated by the method. The invention also relates to a method for treatment of cancer and infectious diseases including AIDS with the activated human antigen-presenting cells, and to a use of the activated human antigen-presenting cells in the preparation of medicines for treating such diseases. The invention can provide a satisfactory therapeutic effect on cancer and infectious diseases including AIDS without the need to pulse the human antigen-presenting cells with tumor antigens.

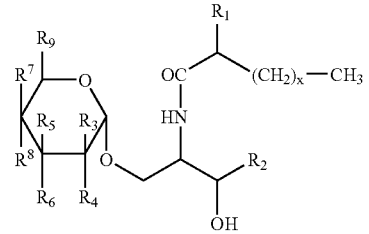

(A)

21 Claims, 14 Drawing Sheets

OTHER PUBLICATIONS

Lars Svennerholm et al., "Sphingolipids of human skeletal muscle.", Biochimica et Biophysica Acta, vol. 280, pp. 626–636, 1972.

K. A. Karlsson et al., "The sphingolipid composition of bovine kidney cortex, medulla and papilla.", Biochimica et Biophysica Acta, vol. 316, pp. 317–335, 1973.*

Masahiro Morita et al., "Structure–activity relationship of α–galactosylceramides against B16–bearing mice.", J. Med. Chem. vol. 38, pp. 2176–2187, 1995.*

Kazuhiro Motoki et al., "Immunostimulatory and antitumor activities of monoglycosylceramides having various sugar moieties.", Biol. Pharm. Bull., vol. 18, No. 11, pp. 1487–1491, 1995.*

Kazuhiro Motoki et al., "Radioprotective effects of α–galactosylceramides.", Bioorganic & Medicinal Chemistry Letters, vol. 5, No. 20, pp. 2413–2416, 1995.*

Kazuhiro Motoki et al., "Effects of α–galactosylceramides on bone marrow cells in vitro and hematopoiesis in vivo.", Biol. Pharm. Bull. vol. 19, No. 7, pp. 952–955, 1996.*

Y. Koezuka et al., "KRN7000, A novel enhancer of antigen presenting cell (APC) activity of dendritic cell (DC).", The 9th International Congress of Immunology, p. 55, Abstract No. 324, 1995.*

Yasunori Yamaguchi et al., "Enhancing effects of (2S, 3S, 4R)–1–0–(α–D–Galactopyranosyl)–2–(N– Hexacosanoylamino)–1, 3,4–Octadecanetriol (KRN7000) on antigen–presenting function of antigen–presenting cells and anti-metastatic activity of KRN7000–pretreated antigen–presenting cells.", Oncology Research, vol. 8, Nos. 10/11, pp. 399–407, 1996.*

* cited by examiner

METHOD FOR ACTIVATING HUMAN ANTIGEN-PRESENTING CELLS, ACTIVATED HUMAN ANTIGEN-PRESENTING CELLS, AND USE THEREOF

The above application is a Divisional application of Ser. No. 09/331,789, filed Jun. 25, 1999 which is a 371 of PCT/JP97/04832 filed Dec. 25, 1997.

BACKGROUND OF THE INVENTION

1. Field of the Invention

The present invention relates to a novel activated human antigen-presenting cell, a method for activating a human antigen-presenting cell in vitro, a method for treating cancer and infectious diseases including AIDS using the activated human antigen-presenting cell, and a use of the activated human antigen-presenting cell in preparing medicines for such treatment.

2. Disclosure of Related Art

There have been various strategies for the therapeutical treatment of cancer patients, including surgical extraction of tumor foci, chemotherapy, radiotherapy and immunotherapy. However, the cure rates of these strategies are not as high as they are expected. Therefore, there exists a strong demand for developing new therapeutic agents and methods which can provide improved cure rates in the treatment of cancer. Macrophages, B cells and dendritic cells, which are members of antigen-presenting cell (APC), have been known to be cells essential for immune response. Recently, an idea that using APCs, particularly dendritic cells, to induce cancer immunity may be effective in treating cancer (Grabbe, S. et al., 1995, Immunol. Today, 16, 117) has attracted much attention.

Several processes for preparing dendritic cells from mouse have been known, such as from the spleen (Clowley, M. et al., 1989, Cell. Immunol., 118, 108), from the bone marrow (Inaba, K. et al., 1992, J. Exp. Med., 176, 1693) and from the epidermis (the epidermis-derived dendritic cells are known as "Langerhans's cells") (Witmer-Pack, M. et al., 1987, J. Exp. Med., 166, 1487). Furthermore, it was demonstrated that pulsing the dendritic cells prepared from the murine bone marrow with tumor antigen and administrating the pulsed dendritic cells into a subject prior to and after the implantation of tumor cells into the subject can elicit tumor immunity (Celluzzi, C. M. et al., 1996, J. Exp. Med., 183, 283; Paglia, P. et al., 1996, J. Exp. Med., 183, 317)

The following processes are known for preparing human APCs, particularly dendritic cells, from peripheral blood or umbilical cord blood: a process in which FcR$^+$ cells, T cells, B cells and NK cells are removed from human peripheral blood using the antibodies against them from peripheral blood monocytes to give APCs (Hsu et al., 1996, Nature Med., 2, 52); and a process in which adherent cells in human peripheral blood monocytes from which CD19$^+$ B cells and CD2$^+$ T cells were removed are cultured with a granulocyte-macrophage colony stimulating factor (GM-CSF) and interleukin 4 (IL-4) for about one week (Sallusto, F. et al., 1994, J. Exp. Med., 179, 1109). It has been reported that such human peripheral blood-derived APCs have both allogeneic and autologous MLR (mixed leukocyte reaction) enhancing effects. On the other hand, for preparing APCs from human umbilical cord blood or bone marrow cells, a process is known where GM-CSF and tumor necrosis factor-α (TNF-α) are used to prepare APCs from CD34$^+$ cells found in umbilical cord blood or bone marrow (Santiago-Schwartz, F. et al., 1992, J. Leukocyte Biol., 52, 274; Caux, C. et al., 1992, Nature, 360, 258). However, although the APCs prepared from human umbilical cord blood or bone marrow cells by such a process as mentioned above have an allogeneic MLR enhancing effect, they have no (Santiago-Schwartz, F. et al.) or, if any, extremely poor (Caux et al.) antologous MLR enhancing effect.

Recently, it has been demonstrated that a therapy with the APCs that had been pulsed with tumor antigens is effective for treating B cell lymphoma patients (Hsu, F. J. et al., 1996, Nature Med., 2, 52). That is, a therapy for B cell lymphoma patients was successfully achieved by culturing APCs prepared from peripheral blood of a B cell lymphoma patient together with B cell lymphoma antigens in vitro and administrating the cultured APCs into the B cell lymphoma patient.

As shown in this exemplary therapy, methods in which APCs are pulsed with tumor antigens may be very effective for treating cancer if the cancer can be clearly identified by their tumor antigens, like B cell lymphoma. However, such methods as mentioned above take enormous time and costs, because the tumor antigens are generally specific to the individual patients and, therefore, must be specified for the respective patients, and the specified tumor antigens must be produced in large quantities to pulse the APCs. Furthermore, since it is impossible for most of the cancer patients to identify their tumor antigens, the range of application of the method in which APCs are pulsed with tumor antigens is limited. In view of the above, in order to apply the therapy with APCs (hereinafter referred to as "the APC therapy") recognized to be a very effective therapy for cancer, to as many patients as possible, there has been a strong demand for development of a method for preparing human APCs effective for treating cancer without the aid of tumor antigens.

Within a living body, various types of β-galactosylceramides and β-glucosylceramides are present, each of which has a sugar linked to a ceramide via a β-linkage (Svennerholm, L. et al., 1972, Biochem. Biophys. Acta., 280, 626; Karlsson, K. A. et al., 1973, Biochim. Biophys. Acta., 316, 317). On the other hand, the inventors have found that α-galactosylceramides have remarkable immunostimulatory properties and anti-tumor properties (Morita, M. et al., 1995, J. Med. Chem., 38, 2176), and that such properties of α-galactosylceramides and α-glucosylceramides are far more potent than those of the corresponding β-anomers (Motoki, K. et al., 1995, Biol. Pharm. Bull., 18, 1487). It was also found that compounds having an α-glycosylceramide structure show a protecting effect against radiation when administered into a living subject (Motoki, K. et al., 1995, Bioorg. Med. Chem. Lett., 5, 2413) and cause an increase in the number of platelets and white blood cells (Motoki, K. et al., 1996, Biol. Pharm. Bull., 19, 952). The inventors also have found that an α-galactosylceramide, KRN7000, can enhance the functions of dendritic cell-rich APCs prepared from the murine spleen, and that the enhanced APCs exhibit an anti-tumor effect when administered into a subject before tumors are implanted into the subject (Koezuka, Y. et al., 1995, The 9$^{th}$ International Congress of Immunology, Abstract, 55; Yamaguchi, Y. et al., 1996, Oncol. Res. 8, 399).

However, the effect of glycoside compounds, such as KRN7000, or salts thereof on APCs rich in dendritic cells from murine bone marrows and Langerhans's cells from murine epidermis has not been clarified. In addition, there is no report on anti-tumor effects of the APCs rich in murine spleen- and bone marrow-derived dendritic cells, which have been stimulated with KRN7000, upon administration into a subject after tumors are implanted into the subject. No effect of glycoside compounds such as KRN7000 or salts thereof on human APCs has also been known.

To address the above-mentioned demands, the present invention provides a novel human APC activating agent which is useful in preparing activated human APCs that exhibit a sufficient therapeutic effect on cancer and various infectious diseases including AIDS without the need to pulse the antigen-presenting cells with tumor antigens, and also provides a method for activating human APCs with such an activating agent.

SUMMARY OF THE INVENTION

The present invention provides a method for activating human APCs, which comprises culturing human-derived APCs in vitro with at least one of glycoside compounds represented by formula (A) or salts thereof:

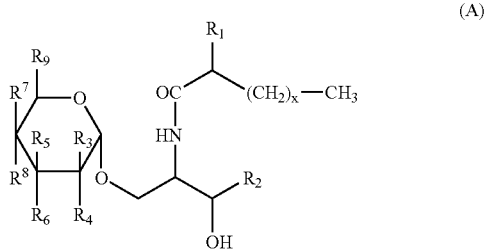

(A)

wherein $R_1$ to $R_9$ and X are to be defined later.

According to one embodiment, the present invention provides a method for activating human APCs which comprises culturing human-derived APCs in vitro with a glycoside compound (2S, 3S, 4R)-1-(α-D-galactopyranosyloxy)-2-hexacosanoylamino-3,4-octadecanediol or a salt thereof.

The present invention also provides activated human APCs which can be prepared by culturing human-derived APCs in vitro with at least one of the glycoside compounds represented by formula (A) above or salts thereof.

The present invention further provides a method for treating cancer and infectious diseases including AIDS, which comprises applying an APC therapy with such activated human APCs as defined above.

The present invention further provides a use of such activated human APCs as defined above in the preparation of a medicine for treating cancer and infectious diseases including AIDS by application of the APC therapy.

BRIEF DESCRIPTION OF THE DRAWINGS

In FIG. 1, "V-APC" and "KRN-APC" refer to human peripheral blood-derived APCs pretreated with a vehicle and KRN7000, respectively.

In FIG. 2, "V-APC" and "KRN-APC" refer to human umbilical cord blood-derived APCs (CD1c$^+$ cells) stimulated with a vehicle and KRN7000, respectively.

In FIG. 3, "V-APC" and "KRN-APC" refer to the same APCs as those used in FIG. 2.

In FIG. 2, "V-APC", "KRN-APC", "583-APC", 517-APC", "564-APC", "563-APC" and "562-APC" refer to murine spleen-derived APCs pretreated with a vehicle, KRN7000, AGL-583, AGL-517, AGL-564, AGL-563 and AGL-562, respectively.

In FIG. 6, "V-APC" and "KRN-APC" refer to murine bone marrow-derived APCs pretreated with a vehicle and KRN7000, respectively.

In FIG. 8, "V-APC" and "KRN-APC" refer to murine epidermis-derived APCs pretreated with a vehicle and KRN7000, respectively.

In FIG. 10, "V-APC", "KRN-APC", "V-APC-GM" and "KRN-APC-GM" refer to human peripheral blood-derived APCs pretreated with a vehicle, KRN7000, a vehicle+GM-CSF+IL4 and KRN+GM-CSF+IL4, respectively.

In FIG. 11, "V-APC-GM" and "KRN-APC-GM" refer to the same APCs as those used in FIG. 10.

In FIG. 12, "V-APC-GM" and "KRN-APC-GM" refer to the same APCs as those used in FIG. 10, and "MCM$^+$" and "MCM$^-$" respectively mean that the APCs are cultured with and without a monocyte conditioned medium (MCM).

In FIG. 13, "V-APC-GM" and "KRN-APC-GM" refer to the human umbilical cord blood-derived APCs respectively pretreated with a vehicle+GM-CSF+IL4 and KRN7000+GM-CSF+IL4.

DETAILED DESCRIPTION OF THE INVENTION

Figure 1:
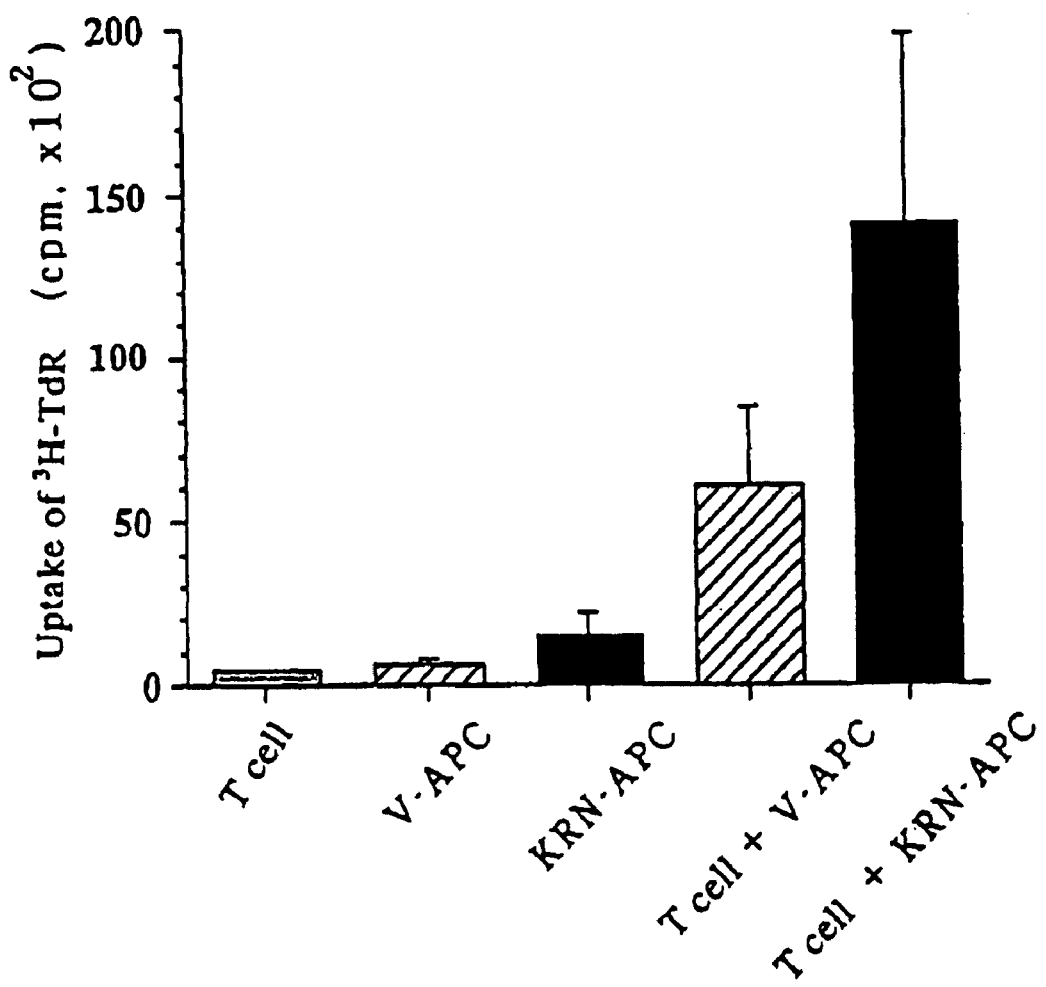
FIG. 1 shows the amount of $^3$H-TdR taken up into the cells variously treated as described.

As a result of extensive and intensive studies by the inventors on the above-mentioned problems, it was found that the glycoside compounds according to the present invention (representatively, KRN7000) can significantly enhance the functions of human APCs prepared from human peripheral blood and human umbilical cord blood. The glycoside compounds can also significantly enhance the functions of dendritic cell-rich APCs from a murine bone marrow and Langerhans's cell-rich APCs from murine auricle, as well as dendritic cell-rich APCs from a murine spleen. It was also found that a significant anti-tumor effect can be observed when dendritic cell-rich APCs from a murine spleen or a murine bone marrow which have been cultured in vitro with the glycoside compounds of the present invention (representatively, KRN7000) are injected into a mouse into which tumor cells have been implanted. Based on these findings, the invention was completed.

That is, the present invention relates to an activating agent (i.e., an antigen-presenting function enhancing agent) comprising a specific glycoside compound, which is useful for preparing activated human APCs having a therapeutic effect on cancer and infectious diseases including AIDS. Specifically, the present invention relates to an activating agent for APCs prepared from human peripheral blood, human umbilical cord blood, human bone marrow cells or human epidermis (i.e., APCs to be activated). More specifically, the present invention relates to an activating agent for human monocytes, human dendritic cells or human $CD1c^+$ cells.

According to the present invention, there is provided a method for activating human antigen-presenting cells which comprises culturing human-derived antigen-presenting cells in vitro with at least one of the glycoside compounds represented by formula (A) or salts thereof:

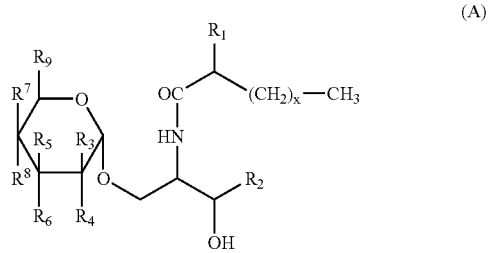

(A)

wherein:
$R_1$ is H or OH;
X is an integer of from 7 to 25;
$R_2$ is a substituent defined by any one of the following (a) to (e):
  (a) —$CH_2(CH_2)_YCH_3$;
  (b) —$CH(OH)(CH_2)_YCH_3$;
  (c) —$CH(OH)(CH_2)_YCH(CH_3)_2$;
  (d) —$CH=CH(CH_2)_YCH_3$; and
  (e) —$CH(OH)(CH_2)_YCH(CH_3)CH_2CH_3$;
    wherein Y is an integer of from 5 to 17;
$R_3$ is H; F
$R_4$ is OH, $NH_2$, $NHCOCH_3$ or

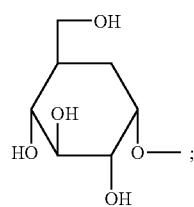

one of $R_5$ and $R_6$ is H and the other is OH,

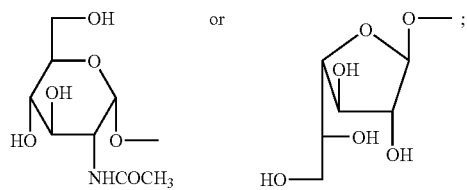

one of $R_7$ and $R_8$ is H and the other is OH

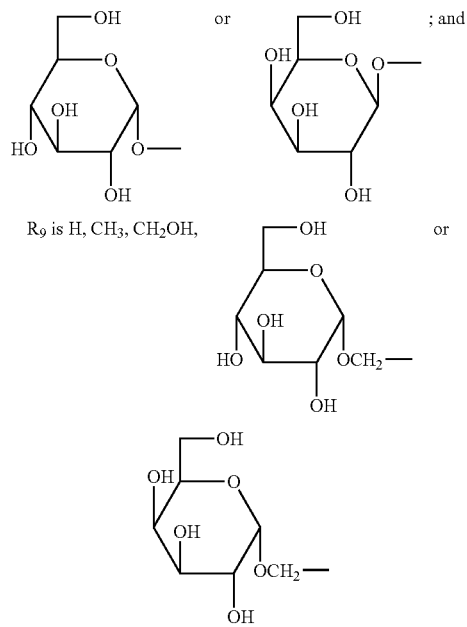

$R_9$ is H, $CH_3$, $CH_2OH$,

In a preferred embodiment, the present invention provide a method for activating human antigen-presenting cells which comprises using at least one of the glycoside compounds represented by formula (B) or salts thereof:

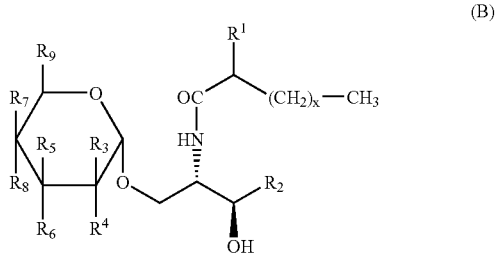

(B)

wherein:

$R_1$, X and $R_2$ are as defined as in the case of formula (A); and $R_3$ to $R_9$ are substituents defined by any one of the following (i) to (iii):
  (i) [galactose type]
  each of $R_3$, $R_6$ and $R_8$ is H;

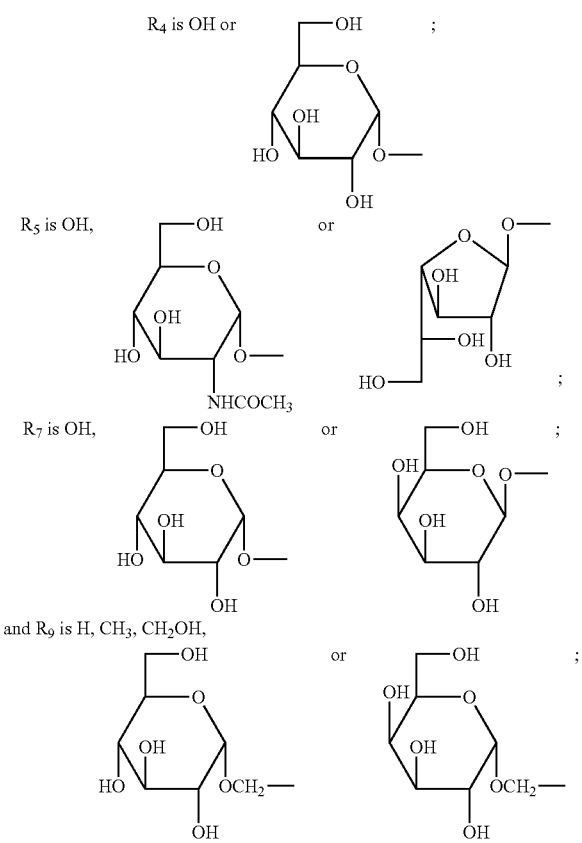

(ii) [glucose type]
each of $R_3$, $R_6$ and $R_7$ is H;
$R_4$, $R_5$ and $R_9$ are as defined as in (i) and

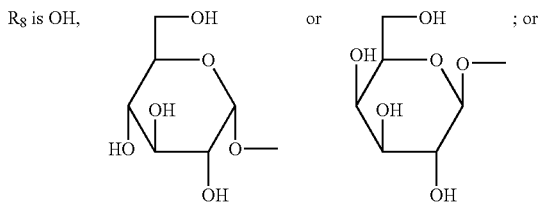

(iii) [allose type]
each of $R_3$, $R_5$ and $R_7$ is H;
each of $R_4$, $R_6$ and $R_8$ is OH; and
$R_9$ is H, $CH_3$ or $CH_2OH$.

The glycoside compounds defined by formula (A) or (B) above are comprised of a sugar moiety and an aglycone moiety, and some of them are also referred to as α-cerebrosides, α-glycosylceramides, α-glucosylceramides, α-galactocerebrosides or α-galactosylceramides. These compounds are characterized by having the α-form of anomeric configuration.

In the glycoside compound, the sugar moiety is preferably of [galactose type] as defined in (i), and more preferably of one wherein each of $R_3$, $R_6$ and $R_8$ is H, each of $R_4$, $R_5$ and $R_7$ is OH and $R_9$ is $CH_2OH$ (i.e., α-galactopyranosyl).

In the glycoside compound, the aglycone moiety preferably has $R_2$ being any one of the substituents (b), (c) and (e) above, and more preferably has $R_1$ being H (i.e., kerasin type) and $R_2$ being the substituent (b). X is preferably an integer of 21 to 25 and Y is preferably an integer of 11 to 15.

Preferable examples of the glycoside compound of the present invention are listed below. In the list, compounds (1)–(9), (10)–(24), (25)–(31), (32)–(33), and (34) are those compounds in which $R_2$ is the substituent (a), (b), (c), (d) or (e) above, respectively. The alphabet letters A, B, C and D behind the compounds' name indicate the reference specifications of WO93/05055, WO94/02168, WO94/09020 and WO94/24142, respectively, which describe the synthesis methods of the annoted compounds. Among the glycoside compounds below, compound (14) (2S,3S,4R)-1-(α-D-galactopyranosyloxy)-2-hexacosanoylamino-3,4-octadecanediol (referred to as "KRN7000" hereinbelow), is most preferable. With respect to this compound, an example of the synthesis process will be illustrated in the Production Example and Scheme 1 below.

| | | |
|---|---|---|
| (1) | (2S,3R)-1-(α-D-galactopyranosyloxy)-2-[(R)-2-hydroxytetracosanoylamino]-3-octadecanol | A |
| (2) | (2S,3R)-1-(α-D-galactopyranosyloxy)-2-tetracosanoylamino]-3-octadecanol | A |
| (3) | (2S,3R)-1-(α-D-galactopyranosyloxy)-2-tetradecanoylamino-3-octadecanol | A |
| (4) | (2S,3R)-1-(α-D-glucopyranosyloxy)-2-tetradecanoylamino-3-octadecanol | C |
| (5) | (2S,3R)-1-(6'-deoxy-α-D-galactopyranosyloxy)-2-tetradecanoylamino-3-octadecanol | C |
| (6) | (2S,3R)-1-(β-L-arabinopyranosyloxy)-2-tetradecanoylamino-3-octadecanol | C |
| (7) | (2S,3R)-1-(α-D-galactopyranosyloxy)-2-tetradecanoylamino-3-hexadecanol | A |
| (8) | (2S,3R)-1-(α-D-galactopyranosyloxy)-2-tetradecanoylamino-3-hexadecanol | A |
| (9) | (2R,3S)-1-(α-D galactopyranosyloxy)-2-tetradecanoylamino-3-hexadecanol | A |
| (10) | (2S,3S,4R)-1-(α-D-galactopyranosyloxy)-2-[(R)-2-hydroxytetracosanoylamino]-3,4-octadecanediol | A |
| (11) | (2S,3S,4R)-1-(α-D-galactopyranosyloxy)-2-[(R)-2-hydroxytetracosanoylamino]-3,4-undecanediol | A |
| (12) | (2S,3S,4R)-1-(α-D-galactopyranosyloxy)-2-[(R)-2-hydroxyhexacosanoylamino]-3,4-icosanediol | A |
| (13) | (2S,3S,4R)-1-(α-D-galactopyranosyloxy)-2-[(S)-2-hydroxytetracosanoylamino]-3,4-heptadecanediol | A |
| (14) | (2S,3S,4R)-1-(α-D-galactopyranosyloxy)-2-hexacosanoylamino-3,4-octadecanediol | Production Example |
| (15) | (2S,3S,4R)-1-(α-D-galactopyranosyloxy)-2-octacosanoylamino-3,4-heptadecanediol | B |
| (16) | (2S,3S,4R)-1-(α-D-galactopyranosyloxy)-2-tetracosanoylamino-3,4-octadecanediol | A |
| (17) | (2S,3S,4R)-1-(α-D-galactopyranosyloxy)-2-tetracosanoylamino-3,4-undecanediol | A |
| (18) | (2S,3S,4R)-1-(α-D-galactopyranosyloxy)-2-hexacosanoylamino-3,4-octadecanediol | C |
| (19) | O-β-D-galactofuranosyl-(1→3)-O-α-D-galactopyranosyl-(1→1)-(2S,3S,4R)-2-amino-N-[(R)-2-hydroxytetracosanoyl]-1,3,4-octadecanetriol | D |
| (20) | O-α-D-galactopyranosyl-(1→6)-O-α-D-glucopyranosyl-(1→1)-(2S,3S,4R)-2-amino-N-hexacosanoyl-1,3,4-octadecanetriol | D |
| (21) | O-α-D-galactopyranosyl-(1→6)-O-α-D-galactopyranosyl-(1→1)-(2S,3S,4R)-2-amino-N-hexacosanoyl-1,3,4-octadecanetriol | D |
| (22) | O-α-D-glucopyranosyl-(1→4)-O-α-D-glucopyranosyl-(1→1)-(2S,3S,4R)-2-amino-N-hexacosanoyl-1,3,4-octadecanetriol | D |
| (23) | O-(N-acetyl-2-amino-2-deoxy-α-D-galactopyranosyl-(1→3)-O-[α-D-glucopyranosyl-(1→2)]-O-α-D-galactopyranosyl-(1→1)-(2S,3S,4R)-2-amino-N-[(R)-2-hydroxyhexacosanoyl]-1,3,4-octadecanetriol | D |
| (24) | O-(N-acetyl-2-amino-2-deoxy-α-D-galactopyranosyl-(1→3)-O-[α-D-glucopyranosyl-(1→2)]-O-α-D-galactopyranosyl-(1→1)-(2S,3S,4R)-2-amino-N-[(R)-2-hydroxytetracosanoyl]-1,3,4-hexadecanediol | D |
| (25) | (2S,3S,4R)-1-(α-D-galactopyranosyloxy)-2-[(R)-2-hydroxytricosanoylamino]-16-methyl-3,4-heptadecanediol | A |

-continued

| | | |
|---|---|---|
| (26) | (2S,3S,4R)-1-(α-D-galactopyranosyloxy)-2-[(S)-2-hydroxytetracosanoylamino]-16-methyl-3,4-heptadecanediol | A |
| (27) | (2S,3S,4R)-1-(α-D-galactopyranosyloxy)-16-methyl-2-tetracosanoylamino]-3,4-heptadecanediol | A |
| (28) | O-β-D-galactofuranosyl-(1→3)-O-α-D-galactopyranosyl-(1→1)-(2S,3S,4R)-2-amino-N-[(R)-2-hydroxytetracosanoyl]-17-methyl-1,3,4-octadecanetriol | D |
| (29) | O-β-D-galactofuranosyl-(1→3)-O-α-D-galactopyranosyl-(1→1)-(2S,3S,4R)-2-amino-N-[(R)-2-hydroxytetracosanoyl]-15-methyl-1,3,4-hexadecanediol | D |
| (30) | O-(N-acetyl-2-amino-2-deoxy-α-D-galactopyranosyl-(1→3)-O-[α-D-glucopyranosyl-(1→2)]-O-α-D-galactopyranosyl-(1→1)-(2S,3S,4R)-2-amino-N-[(R)-2-hydroxyhexacosanoyl-16-methyl-1,3,4-octadecanetriol | D |
| (31) | O-(N-acetyl-2-amino-2-deoxy-α-D-galactopyranosyl-(1→3)-O-[α-D-glucopyranosyl-(1→2)]-O-α-D-galactopyranosyl-(1→1)-(2S,3S,4R)-2-amino-N-[(R)-2-hydroxytetracosanoyl-16-methyl-1,3,4-heptadecanetriol | D |
| (32) | (2S,3S,4E)-1-(α-D-galactopyranosyloxy)-2-octadecanoylamino-4-octadecene-3-ol | A |
| (33) | (2S,3S,4E)-1-(α-D-galactopyranosyloxy)-2-tetradecanoylamino-4-octadecene-3-ol | A |
| (34) | (2S,3S,4R)-1-(α-D-galactopyranosyloxy)-2-[(R)-2-hydroxypentacosanoylamino]-16-methyl-3,4-octadecanediol | A |

The glycoside compound defined by formula (A) or (B) may form an acid addition salt with a pharmaceutically acceptable acid. Examples of the acid to be used for formation of such an acid addition salt include inorganic acids such as hydrochloric acid, sulfuric acid, nitric acid and phosphoric acid; and organic acids such as acetic acid, propionic acid, maleic acid, oleic acid, palmitic acid, citric acid, succinic acid, tartaric acid, fumaric acid, glutamic acid, pantothenic acid, lauryl sulfonic acid, methanesulfonic acid and phthalic acid.

The human APC-activating agent according to the present invention can be used to activate the APCs prepared from various human tissues such as peripheral blood, umbilical cord blood, bone marrow cells and epidermis. Typically, the activating agent of the present invention can be added in vitro during or after the preparation of the human APCs (for example, from human peripheral blood, umbilical cord blood or bone marrow cells and, if necessary, with GM-CSF and IL-4) to give the activated human APCs. The activated human APCs may be prepared more efficiently by adding substance(s) such as SCF, IL-1, IL-3, TNF-α and Flk2/Flt3 ligand or a monocyte conditioned medium (MCM) in addition to GM-CSF and IL-4. Moreover, in the preparation of the activated human APCs, tumor antigens, viral antigens or antigen-specific peptides thereof can be added to give the activated human APCs that are more effective for treating cancer and infectious diseases.

The human APC-activating agent of the present invention may be dissolved in an appropriate dissolving solvent such as DMSO and then diluted to an appropriate concentration with physiological saline, a culture medium or the like. The final concentration of the activating agent in a suitable cultivation for activating human APCs is within the range from 0.1 ng/mL to 10 µg/mL, and preferably from 0.01 µg/mL to 1 µg/mL. It is preferable that the human APC-activating agent according to the present invention be prepared and added immediately before it is used.

Accordingly, the present invention also provides activated human APCs which can be prepared by culturing human-derived APCs in vitro with at least one of the glycoside compounds represented by formula (A) or (B) defined above or salts thereof.

In an embodiment of the present invention, the human-derived APCs are CD1c-positive or CD1c-rich cells. Such cells may be prepared from, but not limited to, human peripheral blood, human umbilical cord blood, human bone marrow cells, human epidermis, and the like.

The use of the human APCs activated with the activating agent of the present invention leads to effective APC therapy for patients suffering from cancer. Furthermore, it is expected that the cytotoxic T lymphocytes (CTLS) prepared by co-culturing the activated APCs and peripheral blood from a patient can be used for an effective therapy for patients suffering from cancer or infectious diseases including AIDS.

Accordingly, the present invention also provides a method for treating cancer and infectious diseases including AIDS with the activated human APCs.

The present invention further provides a use of the activated human APCs in the preparation of medicines for treating cancer and infectious diseases including AIDS by application of an APC therapy.

The following examples illustrate the present invention more clearly; however, these examples are not be construed to limit the scope of the invention.

EXAMPLES

Production Examples

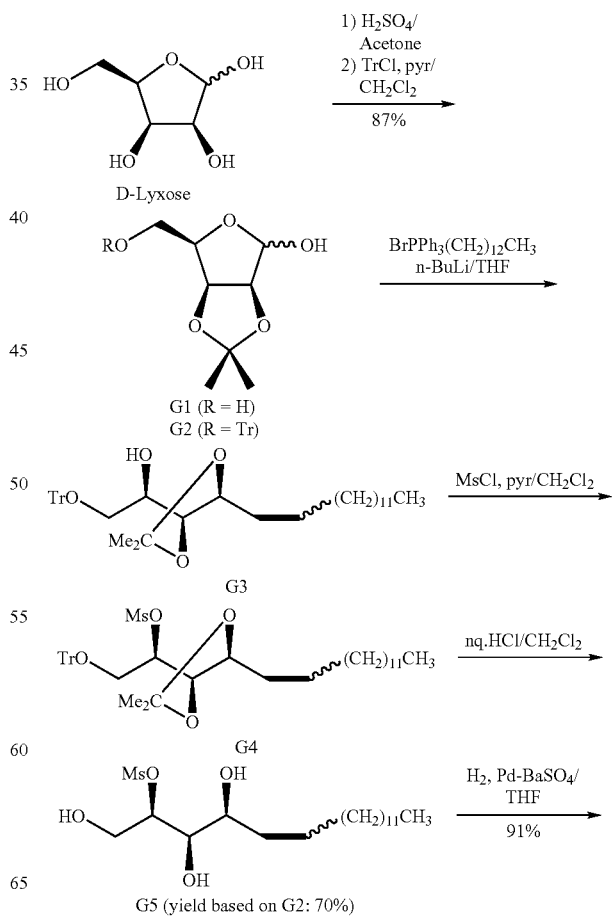

SCHEME 1

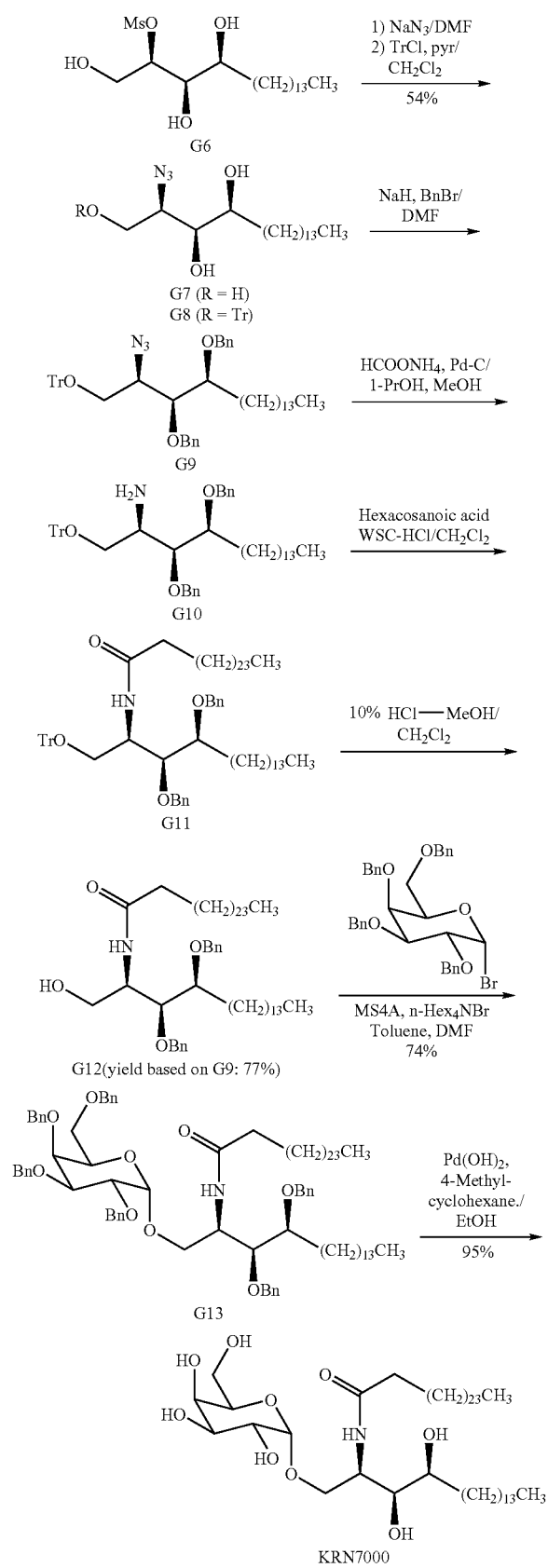

Synthesis of Compound G1

To a solution of D-lyxose (200 g, 1.33 mol) in acetone (3.0 L) dried over calcium chloride was added sulfuric acid (0.5 mL). The mixture was stirred at room temperature for 18 hours, and Molecular Sieves 4A powder (100 g) was then added thereto. After neutralizing, the reaction solution was filtered with celite and the residue was washed with acetone. The filtrate and the washings were combined and concentrated under reduced pressure, thereby giving a crude product of Compound G1 in an amount of 240 g (yield 95%). For the subsequent reaction, the crude product was used without any further purification. For the preparation of a sample for analyses, a portion of the crude product was subjected to further purification by chromatography on a silica gel column with hexane:acetone (9:1) as an eluent.

mp 76–78° C.; FDMS m/z 191 (M+1)$^+$; $^1$H-NMR (500 MHz, CDCl$_3$) δ5.45 (1H, d, J=1.8 Hz), 4.83(1H, dd, J=3.7, 5.5 Hz), 4.64 (1H, d, J=6.1 Hz), 4.27–4.30(1H, m), 3.90–3.99(2H, m) 1.48 (3H, s), 1.32 (3H, s).

Synthesis of Compound G2

To a solution (168 mL) of Compound G1 (239 g, about 1.26 mol) in methylene chloride were added pyridine (10 mL) and trityl chloride (39.0 g), and the mixture was stirred at 32° C. for 4 hours. Ethanol (8 mL) was then added to the solution dropwise and stirred at room temperature for 2 hours. The solution was washed with a saturated aqueous ammonium chloride solution, a saturated aqueous sodium hydrogencarbonate solution and the brine, and was concentrated under reduced pressure. The residue was dissolved in ethyl acetate and then cooled to 0° C. to cause precipitation, thereby giving a product of Compound G2 in an amount of 501 g (yield based on the amount of D-lyxose: 87%).

mp 174–176° C.; FDMS m/z 432 M$^+$; $^1$H-NMR (500 MHz, CDCl$_3$) δ7.21–7.49 (15H, m), 5.38(1H, d, J=2.4 Hz), 4.75(1H, dd, J=3.7, 6.1 Hz), 4.59(1H, d, J=6.1 Hz), 4.31–4.35(1H, m), 3.43(1H, dd, J=4.9, 9.8 Hz), 3.39(1H, dd, J=6.7, 9.8 Hz), 1.29(3H, s), 1.28(3H, s).

Synthesis Compound G3

To a solution (1500 mL) of tridecanetriphenylphosphonium bromide (962 g, 1.16 mol; a product prepared by heating 1-bromotridecane and triphenylphosphine at 140° C. for 4.5 hours) in THF was added a 2.5 M solution of n-butyl lithium in hexane (462 mL, 1.16 mol) dropwise in an atmosphere of argon at 0° C. After the dropwise addition was completed, the resultant solution was stirred for 15 minutes. To the solution was added a solution (450 mL) of Compound G2 (250 g, 579 mmol) in THF dropwise. The resultant solution was stirred for 18 hours while gradually elevating the solution temperature to room temperature. The reaction solution was concentrated under reduced pressure. To the residue was added a mixed solution of hexane:methanol:water (10:7:3, 1000 mL) and washed with a saturated aqueous ammonium chloride solution. The aqueous layer was extracted with hexane (500 mL) several times. All of the organic layers obtained were combined, dried over anhydrous magnesium sulfate, and then concentrated under reduced pressure, thereby giving a crude product of Compound G3 in an amount of 339 g (yield: 98%). For the subsequent reaction, the crude product was used without any further purification. For the preparation of a sample for analyses, a portion of the crude product was subjected to further purification by chromatography on a silica gel column with hexane:ethyl acetate (9:1) as an eluent.

FDMS m/z 598M$^+$; $^1$H-NMR (500 MHz, CDCl$_3$) δ7.21–7.45 (15H, m), 5.48–5.59(2H, m), 4.91(0.7H, t, J=7.3 Hz), 4.44(0.3H, t, J=7.3 Hz), 4.26(0.3H, dd, J=4.3, 7.3 Hz), 4.21(0.7H, dd, J=4.3, 6.7 Hz), 3.75(0.7H, m), 3.69(0.3H, m), 3.24(0.3H, dd, J=4.9, 9.8 Hz), 3.17(0.7H, dd, J=4.9, 9.8 Hz), 3.09–3.14 (1H, (3.11, dd, J=4.9, 9.2 Hz), H1bE overlapped), 1.75–2.03(2H, m), 1.49(3H, s), 1.39 and 1.38(3H, each s), 1.21–1.34(20H, m), 0.88(3H, t, J=6.7 Hz).

Synthesis of Compound 4

To a solution (1500 mL) of Compound G3 (338 g, about 565 mmol) in methylene chloride was added pyridine (500 mL). Subsequently methanesulfonyl chloride (49 mL, 633 mmol) was added dropwise thereto and then stirred at 31° C. for 24 hours. Ethanol (40 mL) was added dropwise thereto and stirred at room temperature for 1 hour. After the reaction solution was concentrated under reduced pressure, a mixed solution of hexane:methanol:water (10:7:3, 1000 mL) was added to the residue to cause separation of the solution into an aqueous layer and an organic layer. The aqueous layer was extracted with hexane (200 mL) 3 times. All of the organic layers obtained were combined, dried over anhydrous magnesium sulfate, and then concentrated under reduced pressure, thereby giving a crude product of Compound G4 in an amount of 363 g (yield: 95%). For the subsequent reaction, the crude product was used without any further purification. For the preparation of a sample for analyses, a portion of the crude product was subjected to further purification by chromatography on a silica gel column with hexane:ethyl acetate (9:1) as an eluent.

FDMS m/z 676M$^+$; $^1$H-NMR (500 MHz, CDCl$_3$) δ7.21–7.47 (15H, m), 5.41(0.7H, ddd, J=5.5, 9.2, 11.0 Hz), 5.32(0.7H, bt, J=11.0 Hz), 5.22 (0.3H, bdd, J=9.2, 15.0 Hz), 5.02(0.3H, dt, J$_t$=7.3 Hz, J$_d$=15.0 Hz), 4.8 (0.7H, ddd, J=3.1, 5.5, 7.9 Hz), 4.73(0.7H, dd, J=5.5, 9.8 Hz), 4.64–4.67 (0.3H, m), 4.61(0.3H, dd, J=5.5, 9.2 Hz), 4.48(0.7, dd, J=5.5, 7.9 Hz), 4.22(0.3H, dd, J=5.5, 9.2 Hz),3.55(0.3H, dd, J=2.4, 11.6 Hz), 3.45(0.7H, dd, J=3.2, 11.0 Hz), 3.06–3.12[4H, (3.12, S), (3.11, S), (3.09, dd, J=3.1, 11.0 Hz)], 1.66–1.82 (2H,m), 1.47 and 1.46 (3H, each s), 1.39 (3H,s), 1.13–1.35 (20H,m), 0.88 (3H, t, J=6.8 Hz).

Synthesis of Compound G5

To a solution (1500 mL) of Compound G4 (362 g, about 536 mmol) in methylene chloride was added methanol (350 mL). Concentrated hydrochloric acid (200 mL) was added to the solution dropwise and then stirred at room temperature for 5 hours. The reaction solution was neutralized with sodium hydrogencarbonate and then subjected to filtration. The filtrate was concentrated under reduced pressure, and ethyl acetate was added to the residue and then washed with brine. The aqueous layer was extracted with ethyl acetate several times. All of the organic layers obtained were combined, dried over anhydrous magnesium sulfate, and then concentrated under reduced pressure. The resultant product was crystallized from hexane to give a product of Compound G5 in an amount of 161 g (yield based on the amount of Compound G2:70%).

mp 66–67° C.; FDMS m/z 377(M-H$_2$O)+; $^1$H-NMR(500 MHz, CDCl$_3$+D$_2$O) δ5.86(0.3H, dt, J$_t$=7.3 Hz, J$_d$=14.7 Hz), 5.77(0.7H, dt, J$_t$=7.3, J$_d$=10.4 Hz), 5.55(0.3H, br.dd, J=7.3, 14.7 Hz), 5.49(0.7H, bt, J=9.8 Hz), 4.91–4.97(1H, m), 4.51 (0.7H, bt, J=9.8 Hz), 4.11(0.3H, bt, J=7.3 Hz), 3.94–4.03 (2H,m), 3.67–3.73 [(1H, (3.70, dd, J=3.1, 6.7 Hz), (3.69, dd, J=3.1, 7.3 Hz)], 3.20 and 3.19 (3H,each s), 2.05–2.22(2H, m), 1.22–1.43(20H,m), 0.88(3H, t, J=6.7 Hz).

Synthesis of Compound G6

To a solution (780 mL) of Compound G5 (160 g, 405 mmol) in THF was added 5% palladium on barium sulfate (16 g). After the reaction vessel was purged with hydrogen gas, the mixture was stirred at room temperature for 20 hours. The reaction solution was filtered with celite and the filter cake was washed with a mixed solution of chloroform:methanol (1:1). The filtrate and the washings were combined and concentrated under reduced pressure. The residue was crystallized from ethyl acetate to give a product of Compound G6 in an amount of 146 g (yield: 91%).

[α]$_{23}$$^D$+12°(c 1, CHCl$_3$/MeOH=1:1); mP 124–126° C.; FDMS m/z 397 (M+1)$^+$; $^1$H-NMR (500 MHz, CDCl$_3$/CD$_3$= 1:1) δ4.93–4.96(1H, m, H2), 3.91(1H, dd, J=6.7, 12.2 Hz), 3.85 (1H, dd, J=4.9, 12.2 Hz), 3.54–3.60(1H, m), 3.50(1H, dd, J=1.8, 8.5 Hz), 3.19(3H, s), 1.75–1.83(1H, m), 1.53–1.62 (1H, m), 1.2–1.45(24H, m), 0.89(3H, t, J=6.7 Hz).

Synthesis of Compound G7

To a solution (1000 mL) of Compound G6 (145 g, 365 mmol) in DMF was added sodium azide (47 g, 730 mmol), and the mixture was stirred at 95° C. for 4 hours. The reaction solution was concentrated. Ethyl acetate (450 mL) was added to the residue, and the resultant solution was washed with water. The aqueous layer was re-extracted with ethyl acetate several times. All of the organic layers obtained were combined, washed with brine, dried over anhydrous magnesium sulfate and then concentrated under reduced pressure, thereby giving a crude product of Compound G7 in an amount of 122 g (yield: 97%). For the subsequent reaction, the crude product was used without any further purification. For the preparation of a sample for analyses, a portion of the crude product was subjected to further purification by chromatography on a silica gel column with hexane:ethyl acetate (9:1) as an eluent.

[α]$_{23}$$^D$+16.5°(c 0.5, CHCl$_3$/MeOH=1:1); mP 92–93° C.; FDMS m/z 344(M+1)$^+$; $^1$H-NMR (500 MHz, CD$_3$OD) δ3.91(1H, dd, J=3.7, 11.6 Hz), 3.75(1H, dd, J=7.9, 11.6 Hz), 3.49–3.61 (3H, m), 1.50–1.71(2H, m), 1.22–1.46(24H,m), 0.90(3H, t, J=6.7 Hz).

Synthesis of Compound G8

To a solution (750 mL) of Compound G7 (121 g, about 352 mmol) in methylene chloride were added pyridine (250 mL) and trityl chloride (124 g, 445 mL), and the mixture was stirred at room temperature for 16 hours. Ethanol (30 mL) was added dropwise thereto and then stirred at room temperature for 30 minutes. After washing with a saturated sodium hydrogencarbonate solution, a saturated aqueous ammonium chloride solution and brine, the reaction solution was dried over anhydrous magnesium sulfate and then concentrated under reduced pressure. The residue was purified by chromatography on a silica gel column with hexane:ethyl acetate (10:1) as an eluent, thereby giving a product of Compound G8 in an amount of 34.4 g (yield based on the amount of Compound G6:52%).

[α]$_{24}$$^D$+11.9°(c 0.9, CHCl$_3$), FDMS m/z 585 M$^+$; $^1$H-NMR (500 MHz, CDCl$_3$+D$_2$0) δ7.24–7.61(15H, m), 3.62–3.66(2H, m) 3.51–3.57(2H, m), 3.42(1H, dd, J=6.0, 10.4 Hz), 1.23–1.56(26H, m), 0.88(3H, t, J=6.7 Hz).

Synthesis of Compound G9

To a solution (300 mL) of Compound G8 (33.5 g, 57.3 mmol) in DMF was added 60% hydrogenated sodium (5.5 g, about 138 mmol in terms of NaH), and the mixture was stirred for 40 minutes. The reaction solution was cooled to 0° C., and then benzyl chloride (15 mL, 120 mmol) was added dropwise thereto. The resultant solution was stirred for 18 hours while gradually elevating the solution temperature to room temperature. Ice-cooled water (100 mL) was added to the reaction solution to stop the reaction, and the reaction solution was then extracted with ethyl acetate. The extract was washed with brine 3 times. All of the organic layers obtained were combined, dried over anhydrous magnesium sulfate, and then concentrated under reduced pressure, thereby giving a crude product of Compound G9 in an amount of 42.2 g (yield: 96%). For the subsequent reaction, the crude product was used without any further purification. For the preparation of a sample for analyses, a portion of the crude product was subjected to further purification by chromatography on a silica gel column with hexane:ethyl acetate (100:1) as an eluent.

$[\alpha]_{24}^D$+9.8°(c 1.0, CHCl$_3$), FDMS m/z 738 (M−N$_2$)+; $^1$H-NMR (500 MHz, CDCl$_3$) δ7.07–7.48(25H, m), 4.57(1H, d, J=11.6 Hz), 4.44(1H, d, J=11.6 Hz), 4.41 (2H, s), 3.73–3.79 (1H, m), 3.46–3.56 (2H, m), 3.37 (1H, dd, J=8.6, 10.4 Hz), 1.20–1.64 (26H, m), 0.88 (3H, t, J=6.7 Hz).

Synthesis of Compounds G10 and G11

To a solution (250 mL) of Compound G9 (41.2 g, about 54 mmol) in 1-propanol was added methanol (30 mL), and subsequently 5% palladium on carbon (4.1 g) and ammonium formate (27.1 g, 4.3 mol) were added thereto. After the mixture was stirred at room temperature for 16 hours, it was diluted with ethyl acetate and then filtered with celite. The filtrate was concentrated under reduced pressure and then dissolved in ethyl acetate. The resultant solution was washed 3 times with a saturated aqueous sodium hydrogencarbonate solution and subsequently with brine. All of the organic layers obtained were combined, dried over anhydrous magnesium sulfate, and then concentrated under reduced pressure, thereby giving a crude product of Compound G10 in an amount of 38.9 g (98%). For the subsequent reaction, the crude product (Compound G10) was used without any further purification.

To a solution (300 mL) of Compound G10 in methylene chloride were added hexacosanic acid (22.4 g, 56.5 mmol) and WSC hydrochloride (12.6 g, 64.6 mmol), and the mixture was refluxed with heating for 2 hours. After cooling to room temperature, the reaction solution was concentrated under reduced pressure. Ethyl acetate (500 mL) was added to the residue, and the resultant solution was washed several times with a 0.5 M aqueous solution of hydrochloric acid, brine, a saturated aqueous sodium hydrogencarbonate solution and then brine. All of the organic layers obtained were combined, dried over anhydrous magnesium sulfate, and then concentrated under reduced pressure, thereby giving a crude product of Compound G11 in an amount of 53.2 g (yield: 88%). For the subsequent reaction, the crude product (Compound G11) was used without any further purification. For the preparation of a sample for analyses, a portion of the crude product was subjected to further purification by chromatography on a silica gel column with hexane:ethyl acetate (100:1) as an eluent.

$[\alpha]_{24}^D$+5.3°(c 0.4, CHCl$_3$); FDMS m/z 1118 M$^+$; $^1$H-NMR (500 MHz, CDCl$_3$) δ7.20–7.38(25H, m), 5.57(1H, d, J=9.1 Hz), 4.80 (1H, d, J=11.6 Hz), 4.48–4.50 (3H, m), 4.24–4.32(1H, m), 3.83 (1H, dd, J=3.0, 6.7 Hz), 3.43–3.51 (2H, m, H1a), 3.29(1H, dd, J=4.3, 9.8 Hz), 1.92(2H, t, J=7.3 Hz), 1.28–1.60(72H, m), 0.88(6H, t, J=6.7 Hz).

Synthesis of Compound G12

To a solution (180 mL) of Compound G11 (52.2 g, about 47 mmol) in methylene chloride was added methanol (36 mL), and a 10% solution of hydrochloric acid in methanol (3.0 mL) was added dropwise thereto. The mixture was stirred at room temperature for 2 hours. The reaction solution was neutralized with sodium hydrogencarbonate powder (18 g) and then filtered with celite. The residue was washed with methylene chloride. The filtrate and the washings were combined, and then washed with brine. The organic layer obtained was dried over anhydrous magnesium sulfate, and then concentrated under reduced pressure. The residue was dissolved in hot acetone and then cooled to 0° C. to cause precipitation of a product of Compound G12 in a purified form in an amount of 38.6 g (yield based on the amount of G9:77%).

$[\alpha]_{24}^D$−29.7°(c 0.7, CHCl$_3$); mp 75–76.5° C.; FDMS m/z 876M$^+$; $^1$H-NMR (500 MHz, CDCl$_3$) δ7.30–7.47(10H, m), 6.03(1H, d, J=7.9 Hz), 4.72 (1H, d, J=11.6 Hz), 4.66(1H, d, J=11.6 Hz), 4.61(1H, d, J=11.6 Hz), 4.45(1H, d, J=11.6 Hz), 4.12–4.17(1H, m), 4.00(1H, dt, J$_t$=4.3, J$_d$=7.3 Hz), 3.67–3.72(2H, m), 3.61(1H, ddd, J=4.3, 8.6, 11.6 Hz), 1.94–2.05(2H, m), 1.15–1.69(72H,m), 0.88(6H, t, J=6.1 Hz).

Synthesis of Compound G13

(1) 2,3,4,6-Tetra-O-benzyl-D-galactopyranosyl acetate (79.8 g) was dissolved in a mixed solution of toluene (160 mL) and isopropyl ether (520 mL) and then cooled to −10–0° C. To the solution was added a solution containing 2.0 equivalent amount of HBr in isopropyl ether (2.8 mmol/mL, about 100 mL). After the reaction solution was stirred at −10–0° C. for about 90 minutes, a 5% aqueous solution of sodium hydrogencarbonate was poured thereto and stirred to neutralize the excess HBr. The whole of the solution was transferred to a separatory funnel to cause separation into an aqueous layer and an organic layer. The aqueous layer obtained was discarded and the organic layer was washed with a 10% aqueous solution of sodium chloride twice. The organic layer was concentrated under reduced pressure, thereby giving a syrup product of 2,3,4,6-tetra-O-benzyl-α-D-galactopyranosyl bromide (Gal-Br).

(2) To a solution (420 mL) containing Compound G12 (60.0 g, 68.6 mmol), tetrahexylammonium bromide (89.4 g, 206 mmol) and Molecular Sieves 4A powder (60 g) in toluene were added DMF (140 mL) and subsequently a solution (250 mL) of Gal-Br (about 137 mmol) in toluene. The mixture was stirred at room temperature for 72 hours. Methanol (12 mL) was added to the reaction solution and stirred for 2 hours. After the solution was filtered with celite, the filtrate was washed with a saturated aqueous sodium hydrogencarbonate solution and brine, dried over anhydrous magnesium sulfate, and then concentrated under reduced pressure. Acetonitrile was added to the residue, and the resultant solution was stirred for 2 hours to cause precipitation. The precipitate obtained was dried under reduced pressure to give a dry powder product. The powder product was purified by chromatography on a silica gel column with hexane:ethyl acetate (8:1) as an eluent, thereby giving Compound G13 in an amount of 70.9 g (yield: 74%).

$[\alpha]_{24}^D$+18.8°(c 0.9, CHCl$_3$); mp 74–75° C.; FDMS m/z 1399 M+1)$^1$; $^1$H-NMR (500 MHz, CDCl$_3$) δ7.21–7.37(30H, m), 6.12 (1H, d, J=9.0 Hz), 4.91(1H, d, J=11.6 Hz), 4.84 (1H, d, J=3.7 Hz), 4.72–4.80 (4H, m), 4.35–4.65 (7H, m), 4.12–4.18 (1H, m), 3.99–4.05(2H, m), 3.84–3.93 (4H, m), 3.73(1H, dd, J=3.7, 11.0 Hz), 3.47–3.51(2H, m), 3.42(1H, dd, J=6.1, 9.1 Hz), 1.87–1.99(2H, m), 1.18–1.70(72H, m), 0.88(6H, t, J=7.4 Hz).

(2S, 3S, 4R)-1-O-(α-D-Galactopyranosyl)-N-hexacosanoyl-2-amino-1, 3, 4-octadecanetriol (KRN7000)

Compound G13 (60.0 g, 42.9 mmol) was suspended into ethanol (960 mL), and a 20% suspension of palladium hydroxide (6.0 g) in ethanol was added thereto. 4-Methylcyclohexene (120 mL, 93.5 mmol) was added to the suspension as a donor compound for hydrogen, and then refluxed under heating for 4 hours. Thereafter, the resultant solution was filtered to remove the catalyst. The residue was washed with hot ethanol. The filtrate was allowed to stand at room temperature to cause precipitation of a white product. The white precipitate was filtered out and then dried under reduced pressure. The powder product obtained was suspended into ethanol:water (92:8, 3.5 L), dissolved by heating while stirring, and then allowed to stand to cause precipitation again. The precipitate solution was filtered and the filter cake obtained was dried under reduced pressure, thereby giving the title compound in a white powder form in an amount of 35.0 g (yield: 95%).

$[\alpha]_{24}^D$+43.6°(c 1.0, pyridine); mp 189.5–190.5° C.; negative FABMS m/z 857(M−N)⁻;IR(cm⁻¹, KBr)3300, 2930, 2850, 1640, 1540, 1470, 1070; ¹H-NMR(500 MHz, $C_5D_5N$) δ8.47(1H, d, J=8.5 Hz), 5.58(1H, d, J=3.7 Hz), 5.27(1H, m), 4.63–4.70 (2H, m), 4.56(1H, m), 4.52(1H, t, J=6.1 Hz), 4.37–4.47 (4H, m), 4.33(2H, m), 2.45(2H, t, J=7.3 Hz), 2.25–2.34(1H, m), 1.87–1.97(2H, m), 1.78–1.85(2H, m), 1.62–1.72(1H, m), 1.26–1.45(66H,m), 0.88(6H, t, J=6.7 Hz). ¹³C-NMR (125 MHz, $C_5D_5N$) δ173.2(s), 101.5(d), 76.7(d), 73.0(d), 72.5(d), 71.6(d), 71.0(d), 70.3(d), 68.7(t), 62.7(t), 51.4(d), 36.8(t), 34.4(t), 32.1(t), 30.4(t), 30.2(t), 30.03(t), 30.00(t), 29.93(t), 29.87(t), 29.81(t), 29.76(t), 29.6 (t), 26.5(t), 26.4(t), 22.9(t), 14.3(q).

PHARMACOLOGICAL TESTS

Pharmacological Test 1

Effect of KRN 7000 on Human Peripheral Blood-derived APC

This experiment was designed to study an effect of KRN7000 (Compound No.14, a representative glycoside compound of the invention) on APCs prepared from human peripheral blood. The APCs (mainly comprised of dendritic cells) derived from human peripheral blood were prepared essentially according to the method of Hsu et al. (supra). Briefly, human peripheral blood was layered over Ficoll-Paque and centrifuged at 2,000 rpm for 35 minutes to give a mononuclear cell fraction. A portion of the mononuclear cell fraction was suspended into PBS ($Ca^{++}$, $Mg^{++}$ free) supplemented with 5% of inactivated human AB serum. The resultant solution was layered over 50% Percol, and then centrifuged at 3,000 rpm for 20 minutes to give a high-density fraction. The high-density fraction was panned using a human γ-globulin-coated dish to remove $FcR^+$ cells therefrom (i.e., a monocyte-removed fraction). The resultant fraction was reacted with anti-CD3 monoclonal antibodies, anti-CD21 monoclonal antibodies and anti-CD56 monoclonal antibodies. After washing, the resultant solution was panned using an anti-mouse IgG antibody-coated dish to remove cells that were reactive with the above antibodies (i.e., T cells, B cells and NK cells). The cell fraction thus obtained (i.e., a fraction from which monocytes, T cells, B cells and NK cells were removed) was cultured in RPMI 1640 medium supplemented with 5% of inactivated human AB serum in the presence of a vehicle (DMSO, final concentration: 0.1%) and KRN7000 (final concentration: 100 ng/mL) for 40 hours. After washing, the resultant cells were provided for use as APCs.

On the other hand, as responder cells, $CD4^+$ T cells were purified from the rest of the above-prepared mononuclear cell fraction using a human $CD4^+$ T cell-enrichment column, and were cultured in RPMI 1640 medium supplemented with 5% of inactivated human AB serum until they were subjected to use with the APCs.

The APCs ($5\times10^4$ cells/well) and the responder cells ($1\times10^5$ cells/well) both prepared in the above steps were added to wells of a 96-well flat-bottomed plate, and then subjected to autologous MLR assay. During the last 12 hours of the 6-day culture period, tritium-thymidine (³H-TdR) was added to each of the wells (0.5 μCi/well), and then the cells were harvested. The amount of the ³H-TdR taken up into the cells was determined using a liquid scintillation counter. The results (mean value and standard deviation of 3 wells) are shown in FIG. 1. In FIG. 1, "V-APC" and "KRN-APC" refer to the APCs pretreated with the vehicle and KRN7000, respectively.

As shown in FIG. 1, when each of $CD4^+$ T cell, the vehicle-pretreated APC (V-APC) and the KRN7000-pretreated APC (KRN-APC) were cultured singly, in either case, the cells took up no or a negligible amount of ³H-TdR. In contrast, when the above-prepared T cell was mixed with V-APC, an obvious ³H-TdR uptake was observed. When the T cell was mixed with KRN-APC, a significantly remarkable ³H-TdR uptake was observed. These results demonstrate that KRN-APC has a more significant autologous MLR enhancing effect than V-APC. Accordingly, KRN7000 has an activating effect on the APCs prepared from human peripheral blood (i.e., an antigen-presenting function enhancing effect).

Pharmacological Test 2

Effect of KRN7000 on Human Umbilical Cord Blood-derived APC

APCs derived from human umbilical cord blood (CD1c positive cells; $CD1c^+$ cells) were prepared in the following manner. That is, human umbilical cord blood was layered over Lymphoprep and centrifuged at 1500 rpm for 20 minutes to give a mononuclear cell fraction. A portion of the mononuclear cell fraction was washed with PBS supplemented with 2% inactivated FBS and 1 mM EDTA twice, and FcR was blocked with human γ-globulin. The solution was reacted with anti-CD1c antibodies, and washed with PBS supplemented with 2% FBS and 1 mM EDTA twice. The solution was further reacted with anti-mouse IgG microbeads, washed with PBS supplemented with 2% FBS and 1 mM EDTA, and then suspended into PBS supplemented with 0.5% BSA and 5 mM EDTA. $CD1c^+$ cells were obtained from the suspension using a MiniMACS magnetic column previously washed with PBS supplemented with 0.5% BSA and 5 mM EDTA. The $CD1c^+$ cells obtained were suspended into RPMI 1640 medium supplemented with 10% inactivated human AB blood serum to adjust its density to $1\times10^6$ cells/mL. The cell suspension was added to wells of a 24-well plate (2 mL/well), and then a vehicle (DMSO, final concentration: 0.1%) or KRN7000 (final concentration: 100 ng/mL) was added to each of the wells. After incubating for 3 days, the plate was washed 3 times and provided for use as APCs.

$CD4^+$ T cells were purified from the rest of the above-prepared mononuclear cell fraction using a human $CD4^+$ T cell-enrichment column. The T cells obtained were suspended into RPMI 1640 medium supplemented with 10% inactivated human AB blood serum to adjust its density to $1\times10^6$ cells/well. The suspension was added to wells of a 24-well plate (2 mL/well) and cultured for 3 days. The T cells thus obtained were used as responder cells for autologous MLR assay. On the other hand, a peripheral blood was collected from a normal volunteer, and $CD4^+$ T cells were purified therefrom using a human $CD4^+$ T cell-enrichment column. The T cells thus obtained was used as responder cells for allogeneic MLR assay. The responder cells ($1\times10^5$ cells/50 mL/well) and the stimulator cells (0, 1000, 10000 cells/50 mL/well) were added to wells of a 96-well flat-bottomed plate, and the plate was incubated. For allogeneic MLR assay, the plate was incubated for 4 days, ³H-TdR was added to each of the wells (0.5 μCi/well). After 20 hours, the cells were harvested and the amount of the ³H-TdR taken up into the cells was determined using a liquid scintillation counter. The results (mean value and standard deviation of 3 wells) are shown in FIG. 2.

For autologous MLR assay, the plate was incubated for 7 days, $^3$H-TdR was added to each of the wells (0.5 µCi/well). After 8 hours, the cells were harvested and the amount of the $^3$H-TdR taken up into the cells was determined using a liquid scintillation counter. The results (mean value and standard deviation of 3 wells) are shown in FIG. 3. In FIGS. 2 and 3, "V-APC" and "KRN-APC" refer to the APCs (CD1c$^+$ cells) pretreated with the vehicle and KRN7000, respectively.

Figure 2:
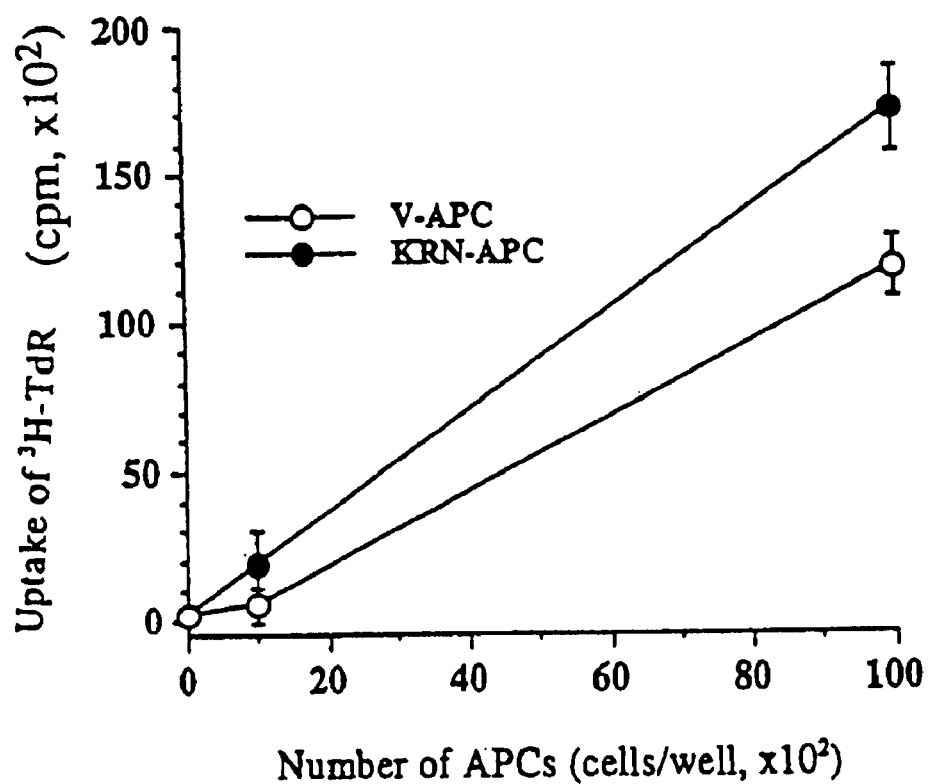
FIG. 2 shows a relationship between the number of APCs and the amount of $^3$H-TdR taken up into an allogeneic T cells.
Figure 3:
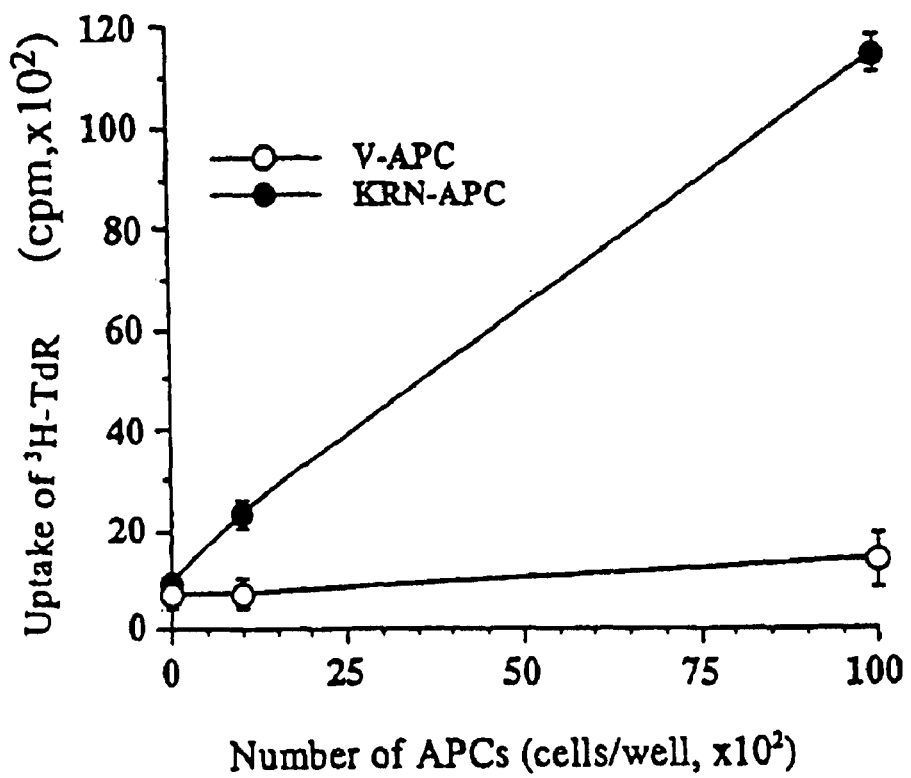
FIG. 3 shows a relationship between the number of APCs and the amount of $^3$H-TdR taken up into autologous T cells.

As shown in FIG. 2., the CD1c$^+$ cells stimulated with the vehicle (APCs; V-APC) promoted the uptake of $^3$H-TdR (proliferation of allogeneic T cells) in a manner dependent on the number of the V-APC, whereas the CD1c$^+$ cells stimulated with KRN7000 (APCs; KRN-APC) showed a stronger allogeneic T cell-proliferation-promoting effect than V-APC.

As shown in FIG. 3, when autologous T cells were used as the responder cells, the CD1c$^+$ cells stimulated with the vehicle (V-APC) hardly stimulated the proliferation of the autologous T cells even if the APCs were added to the wells in an amount of 10000 cells/well; whereas the CD1c$^+$ cells treated with KRN7000 (KRN-APC) significantly stimulated the proliferation of the autologous T cells in a manner dependent on the number of the APCs, similar to the case for the allogeneic T cells.

Pharmacological Test 3

Effect of α- and β-galactosylceramides and α- and β-glucosylceramides on Murine Spleen-derived APC The preparation of dendritic cell-rich APCs from a murine spleen was performed essentially in accordance with the method of Clowley, M. et al. (supra). Briefly, the spleen was removed from a BDF1 mouse. After the treatment with 100 U/mL of collagenase, the spleen was dissected with tweezers to separate into a cell suspension and a tissue debris. The tissue debris was suspended into a 400 U/mL solution of collagenase. After culturing in a $CO_2$ incubator for 20 minutes, the suspension was passed through a stainless steel mesh with an inner syringe to give a cell suspension. Two of the cell suspensions were combined, and subjected to centrifugation. The cell suspension was subjected to density gradient centrifugation with a high-density BSA to give a low-density cell fraction. The cell fraction was plated onto a 60 mm dish and cultured for 2 hours. The procedure for removing the floating cells was repeated 3 times. RPMI 1640 medium supplemented with 10% inactivated FBS was added to the dish and subsequently any one of KRN7000 (Compound No.14), AGL583 (a β-anomer of KRN7000), AGL517 (Compound No.3), AGL564 (a β-anomer of AGL517), AGL563 (Compound No.4), AGL562 (a β-anomer of AGL-563) and a vehicle (DMSO, final concentration: 0.1%) was also added thereto to a final concentration of 100 ng/mL. After culturing overnight, the non-adherent cells were collected, and the resultant cells were provided for use as APCs.

On the other hand, BDF1 mouse spleen cells were treated with a red blood cell-lysing buffer comprised of $NH_4Cl$ and Tris-HCl to hemolyze red blood cells, and the resultant spleen cells were suspended into RPMI 1640 medium supplemented with 10% inactivated FBS. The spleen cells were inoculated onto a 100 mm dish, and cultured in a $CO_2$ incubator for 2 hours. Thereafter, the non-adherent cells were recovered, which were provided for use as responder cells.

The above-prepared APCs ($1 \times 10^3$, $3.3 \times 10^3$ or $1 \times 10^4$ cells/well) and the responder cells ($2.5 \times 10^5$ cells/well) were added to wells of a 96-well plate for syngeneic MLR assay. After culturing for 1 day, $^3$H-TdR was added to each of the wells (0.5 µCi/well). After 16 hours, the cells were harvested, and the amount of 3H-TdR taken up into the cells was determined using a liquid scintillation counter. The results (mean value and standard deviation of 3 wells) are shown in FIG. 4.

Figure 4:
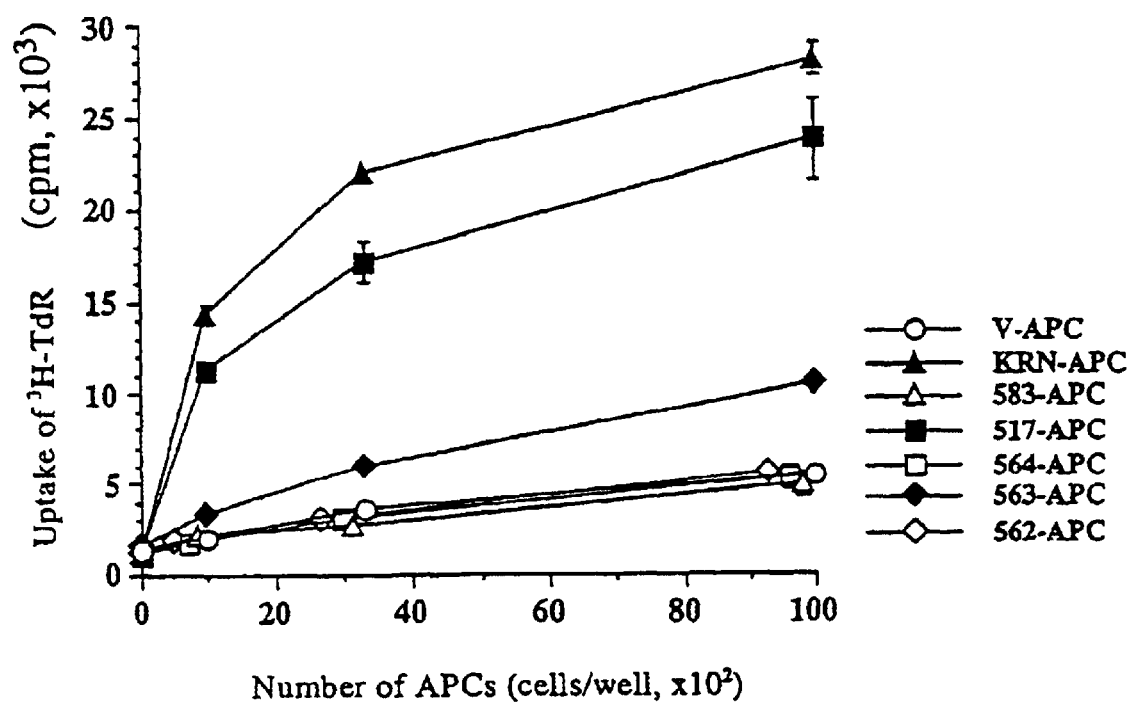
FIG. 4 shows a relationship between the number of APCs and the amount of $^3$H-TdR taken up into spleen cells.

In FIG. 4, "V-APC", "KRN-APC", "583-APC", "517-APC", "564-APC", "563-APC" and "562-APC" refer to the APCs pretreated with the vehicle, KRN7000, AGL-583, AGL-517, AGL-564, AGL-563 and AGL-562, respectively.

As shown in FIG. 4, the APCs pretreated with α-galactosylceramides such as KRN-APC and 517-APV showed a significant syngeneic MLR enhancing effect, whereas the APCs pretreated with β-galactosylceramides such as 583-APC and 564-APC did not show any such effect. The APCs pretreated with α-glucosylceramides such as 563-APC also showed a remarkable syngeneic MLR enhancing effect, whereas the APCs pretreated with β-glucosylceramides such as 562-APC did not show any such effect.

Pharmacological Test 4

APC Therapy with Murine Speen-derived APCs Pertreated with KRN7000

To study an anti-tumor effect of murine spleen-derived APCs activated with KRN7000 on mice implanted with tumor cells, experiments were performed with BDF1 mice (6-week-old, female). All experiments included 6 mice per group. Murine T cell lymphoma EL-4 cells were injected intravenously into each mouse at a level of $1 \times 10^5$ cells/mouse (injection day: day 0). On day 1, the vehicle-pretreated APCs (V-APC) and the KRN7000-pretreated (100 ng/mL) APCs (KRN-APC) both prepared in the same manner as in Pharmacological Test 3 were each injected intravenously into the mice at a level of $5 \times 10^5$ cells/mouse. As a positive control, KRN7000 was injected intravenously into the mice at a dose of 100 µg/kg on days 1, 5 and 9. Each mouse was checked for a sign of life daily to determine its survival period. The results are shown in FIG. 5.

Figure 5:
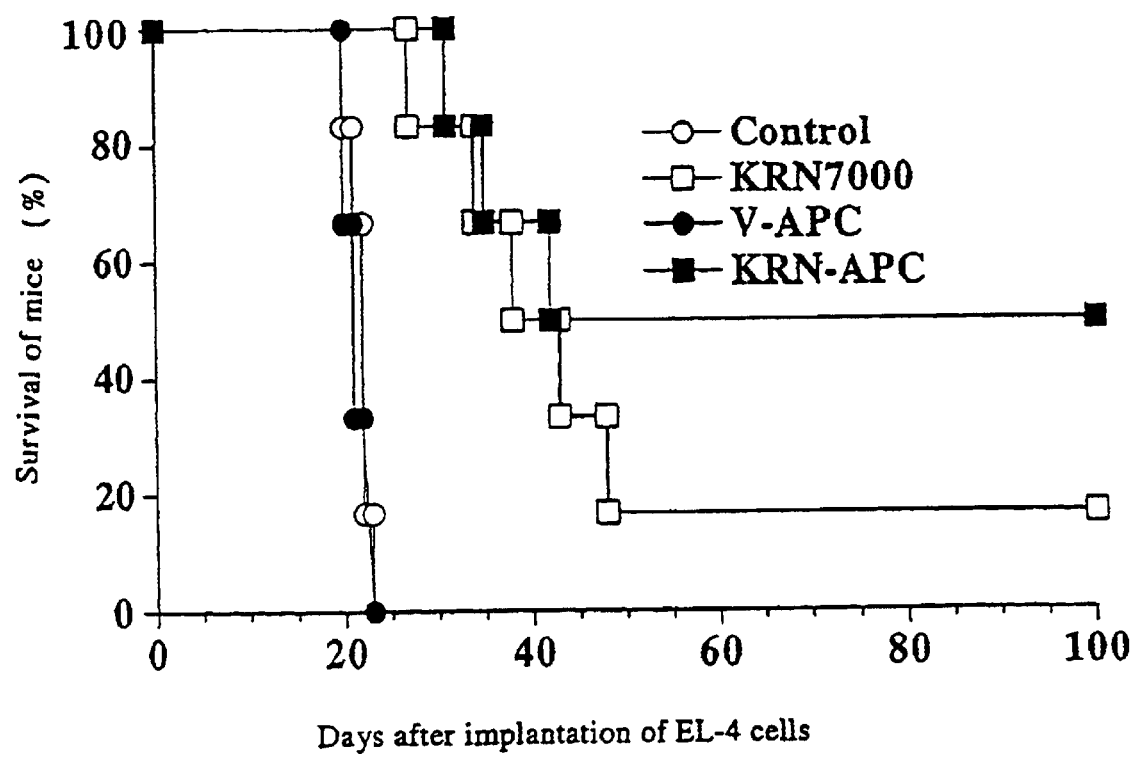
FIG. 5 shows the survival periods of EL-4-bearing mice when murine spleen-derived APCs pretreated with a vehicle or KRN7000 were injected intravenously to the mice.

As shown in FIG. 5, when V-APC was injected, no prolongation of survival period was observed. However, when KRN-APC was injected, a remarkable increase in survival period was observed and 50% of the KRN-APC-injected mice were cured completely. When KRN7000 was injected intravenously at a dose of 100 µg/kg 3 times, a remarkable increase in survival period was observed, however, it was found that the potency of the effect was weaker than that when KRN-APC was injected only once.

Pharmacological Test 5

Figure 6:
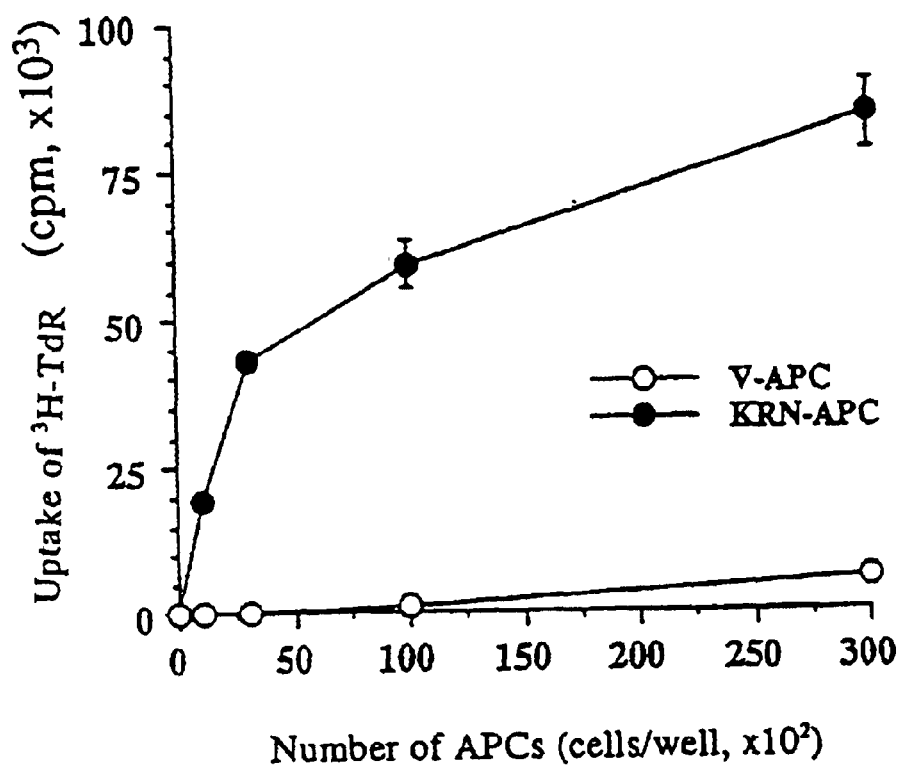
FIG. 6 shows a relationship between the number of APCs and the amount of $^3$H-TdR taken up into T cells.

Antigen Presenting Function Enhancing Effect of KRN700 on Murine Home Marrow-derived Dendritic Cell Dendritic Cell-rich APCs derived from murine bone marrow were prepared according to the method of Inaba, K. et al. (supra) with some modifications (Yamaguchi Y. et al., Stem Cells, 1977:15:144–153). Briefly, bone marrow cells from BALB/c mice were prepared. After hemolyzing the red blood cells with a $NH_4Cl$ solution, FcR$^+$ cells were removed by panning using a human γ-globulin-coated dish. The cells thus obtained were suspended in RPMI medium supplemented with 10% FCS, and cultured in the presence of 10 ng/mL of mouse rGM-CSF and 10 ng/mL of human rTGF-β for 6 days at $5 \times 10^5$ cells/well (1 ml/well, a 24-well plate). Every 2 days, each well was washed briefly using a Pasteur pipette and then about 75% of the medium was sucked out and supplemented with 1 ml of a fresh medium containing the above factors. After culturing for 6 days, non-adherent cells were recovered, and FcR+ cells were removed therefrom by panning using a human γ-globulin-coated dish. The cells thus prepared were cultured in a culture medium supplemented with 10 ng/mL of mouse rGM-CSF and 10 ng/mL of human rTNF-α for additional 2 days. During this culture, either a vehicle (DMSO, final concentration: 0.1%) or KRN7000 (final concentration: 100 ng/mL) was added to the culture medium. The cells were collected and washed 3 times to provide for use as APCS. On the other hand, as responder cells, T cells were prepared from a BALB/c murine spleen using a T cell enrichment column (R&D). T cells were added to wells of a 96-well plate ($3 \times 10^5$ cells/well), and the above-prepared APCs were further added thereto for syngeneic MLR assay ($3 \times 10^4$, $1 \times 10^4$, $3 \times 10^3$ and $1 \times 10^3$ cells/well, respectively). After culturing for 2 days, $^3$H-TdR was added to each of the wells (0.5 μCi/mL). After 6 hours, the cells were harvested and determined on the uptake of $^3$H-TdR into the cells using a liquid scintillation counter. The results (mean value and standard deviation of 3 wells) are shown in FIG. 6. In FIG. 6, "V-APC" and "KRN-APC" refer to the APCs pretreated with the vehicle and KRN7000, respectively.

As shown in FIG. 6, the murine bone marrow-derived APCs which were stimulated with KRN7000 (KRN-APC) showed a remarkable syngeneic MLR enhancing effect compared to the APCs stimulated with the vehicle (V-APC).

Pharmacological Test 6

APC Therapy with Murine Bone Marrow Derived-APCs Pretreated with KRN7000

Figure 7:
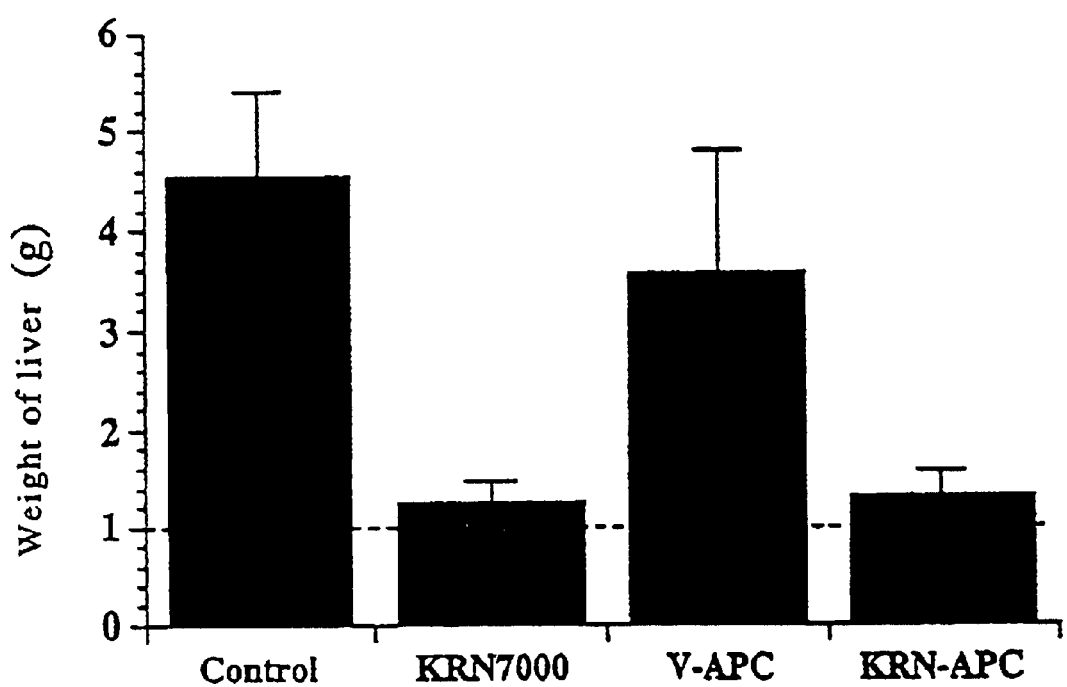
FIG. 7 shows the weight of the liver of a tumor-bearing mouse when the V-APC or KRN-APC prepared in the same manner as in FIG. 6 was injected intravenously into the mouse.

The experiment was performed to study an anti-tumor effect of murine bone marrow-derived APCs activated with KRN7000 on mice implanted with tumor cells. All experiments were performed with CDF1 mice (6-week-old, female), which were divided into groups consisting of 5 mice. Murine colon adenocarcinoma Colon26 cells were implanted into each mouse intrasplenically at a level of $2 \times 10^6$ cells/mouse (inoculation day: day 0). On day 1, the vehicle-pretreated APCs (V-APC) and the KRN7000-pretreated (100 ng/mL) APCs (KRN-APC) both prepared in the same manner as in Pharmacological Test 5 were individually injected intravenously to the mice at a level of $8 \times 10^5$ cells/mouse. As a positive control, KRN7000 was injected intravenously to the mice at a dose of 100 μg/kg on days 1, 5 and 9. On day 14, the liver was removed from each of the mice and weighed. The results (mean value and standard deviation of the weights of the liver of 5 mice) are shown in FIG. 7. Here, the liver from the mouse that had not been implanted with the tumor cells was about 1 g. Accordingly, the substantial tumor weight was determined by subtracting 1 g from the weight of the liver of the tumor-implanted mouse.

As shown in FIG. 7, when V-APC was injected, a slight suppressive effect on tumor growth was observed; whereas when KRN-APC was injected, a remarkable inhibitory effect on tumor growth was observed and no tumor nodule in the liver was observed by naked eyes in 3 of the 5 mice. When KRN7000 was injected intravenously 3 times at a dose of 100 μg/kg, a remarkable inhibitory effect on tumor growth was observed, which was at the same level as that when KRN-APC was injected once.

Pharmacological Test 7

Antigen Presenting Function Enhancing Effect of XRN7000 on Murine Epidermis-derived APCs Langerhans's cell-rich APCs were prepared from murine auricle essentially in accordance with the method of Witmer-Pack, M. et al. (supra). Briefly, the epidermis of auricle of a BALB/c mouse was peeled into front and back epidermal sheets, and each of the epidermal sheets was soaked into Hanks's solution supplemented with 1% trypsin at 37° C. for 30 minutes to 1 hour. The epidermal sheets obtained were placed on a mesh, and shaken up and down in Hanks's solution supplemented with 10% FCS. The cells detached from the epidermal sheets were collected, and then suspended into RPMI solution supplemented with 10% FCS at $10^6$ cells/mL. After addition of either a vehicle (DMSO, final concentration: 0.1%) or KRN7000 (final concentration: 100 ng/mL), the cells were cultured under 5% $CO_2$ at 37° C. for 3 days. Thereafter, the cells that were non-adherent to the dish were collected and layered over Lympholite-M. After centrifugation at 1400 rpm for 10 minutes, the low-density cells were collected, washed with RPMI twice, which were provided for use as APCs.

Figure 8:
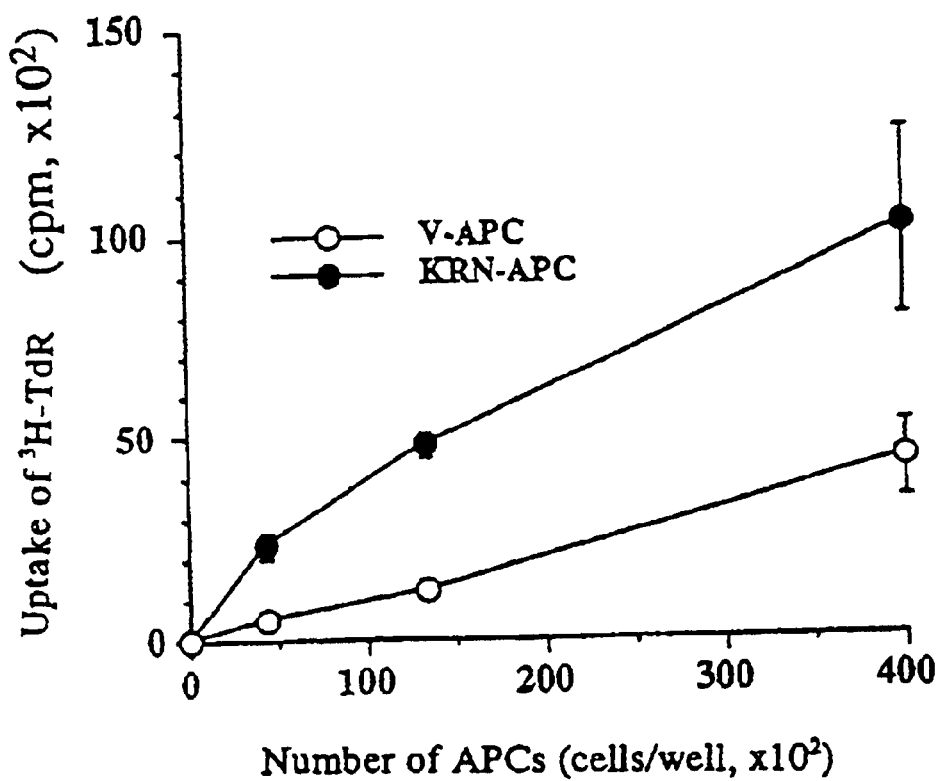
FIG. 8 shows a relationship between the number of APCs and the amount of $^3$H-TdR taken up into spleen cells.

As responder cells, spleen cells were prepared from BALB/c mice in the same manner as described in Pharmacological Test 3. The responder cells thus obtained were added to wells of a 96-well plate ($2.5 \times 10^5$ cells/well), and the APCs were also added thereto for syngeneic MLR assay ($4 \times 10^4$, $4/3 \times 10^4$ and $4/9 \times 10^4$ cells/well, respectively). After culturing for 2 days, $^3$H-TdR was added to each well (0.5 μCi/mL). After 6 hours, the cells were harvested and determined on the amount of $^3$H-TdR taken up into the cells using a liquid scintillation counter. The results (mean value and standard deviation of 3 wells) are shown in FIG. 8. In FIG. 8, "V-APC" and "KRN-APC" refer to the APCs pretreated with the vehicle and KRN7000, respectively.

As shown in FIG. 8, the murine epidermis-derived APCs stimulated with KRN (KRN-APCs) showed a more remarkable syngeneic MLR enhancing effect compared to those stimulated with the vehicle (V-APCs).

Pharmacological Test 8

APC Therapy with Murine Spleen-derived APCs Pertreated with KRN7000 and Tumor Antigen The experiment was performed with BDF1 mice (6-week-old, female), which were divided into groups consisting of 6 mice. Murine melanoma B16 cells were implanted subcutaneously into each mouse at a level of $1.5 \times 10^6$ cells/mouse (implantation day: day 0). Several types of pretreated APCs were prepared in the same manner as in Pharmacological Test 3, in which APCs were pretreated with a vehicle (DMSO, final concentration: 0.1%) (V-APC), with both the vehicle (DMSO, final concentration: 0.1%) and a B16-tumor cell lysate (V-T-APC), with KRN7000 (final concentration: 100 ng/mL) (KRN-APC), and with both KRN7000 (final concentration: 100 ng/mL) and a B16-tumor cell lysate (KRN-T-APC), respectively. Each of the pretreated APCs was injected intravenously into the mice at a dose of $5 \times 10^5$ cells/mouse on day 1. As a positive control, KRN7000 was injected intravenously into the mice at a dose of 100 μg/kg on days 1, 5 and 9. The volume of the subcutaneous tumor in each mouse was measured. The results (the average of the tumor volumes of 6 mice) are shown in FIG. 9.

Figure 9:
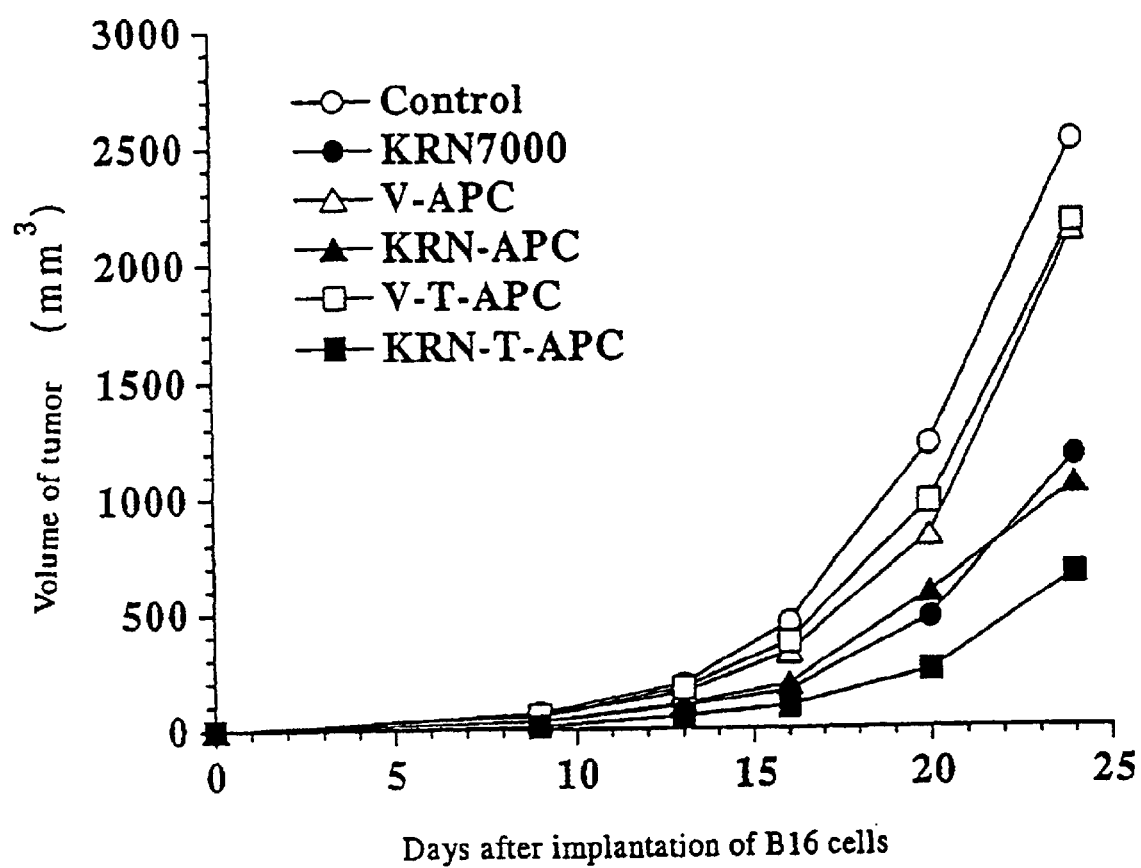
FIG. 9 shows the volume of a subcutaneous tumor for each of the tumor-bearing mice when the APCs pretreated with a vehicle, a vehicle+B16–tumor cell lysate, KRN7000 or KRN7000+B16-tumor cell lysate (V-APC, V-T-APC, KRN-APC or KRN-T-APC, respectively), respectively, was injected intravenously to the mice.

As shown in FIG. 9, little or no tumor growth-suppressive effect was observed when V-APCs and V-T-APCs were injected. On the contrary, when KRN-APCs were injected once, a tumor growth-inhibitory effect was observed, which was at the same level as that when KRN7000 was injected 3 times intravenously at a dose of 100 µg/kg. It is interesting to note that the one injection of KRN-T-APC produced a more remarkable tumor growth inhibitory effect than the one injection of KRN-APC or the three intravenous injections of KRN7000 at a dose of 100 µg/kg.

Pharmacological Test 9

Effect of KRN7000 on Human Peripheral Blood-derived APCs

A monocyte fraction was prepared from human peripheral blood mononuclear cells by Percol density-gradient centrifugation. The monocyte fraction was cultured in the presence or absence of GM-CSF (50 ng/mL) and IL-4 (100 ng/mL), and simultaneously either a vehicle (v; DMSO, 0.1%) or KRN7000 (KRN; 100 ng/mL) was added thereto. After culturing for 3 days, the cells were collected and washed with the medium 3 times to give V-APC, KRN-APC, V-APC-GM and KRN-APC-GM (where "GM" refers to the APCs cultured in the presence of GM-CSF and IL-4), which were then provided for use as APCs. As responder cells, human peripheral blood-derived FcR$^-$ cells were used to perform allogeneic MLR assay.

Figure 10:
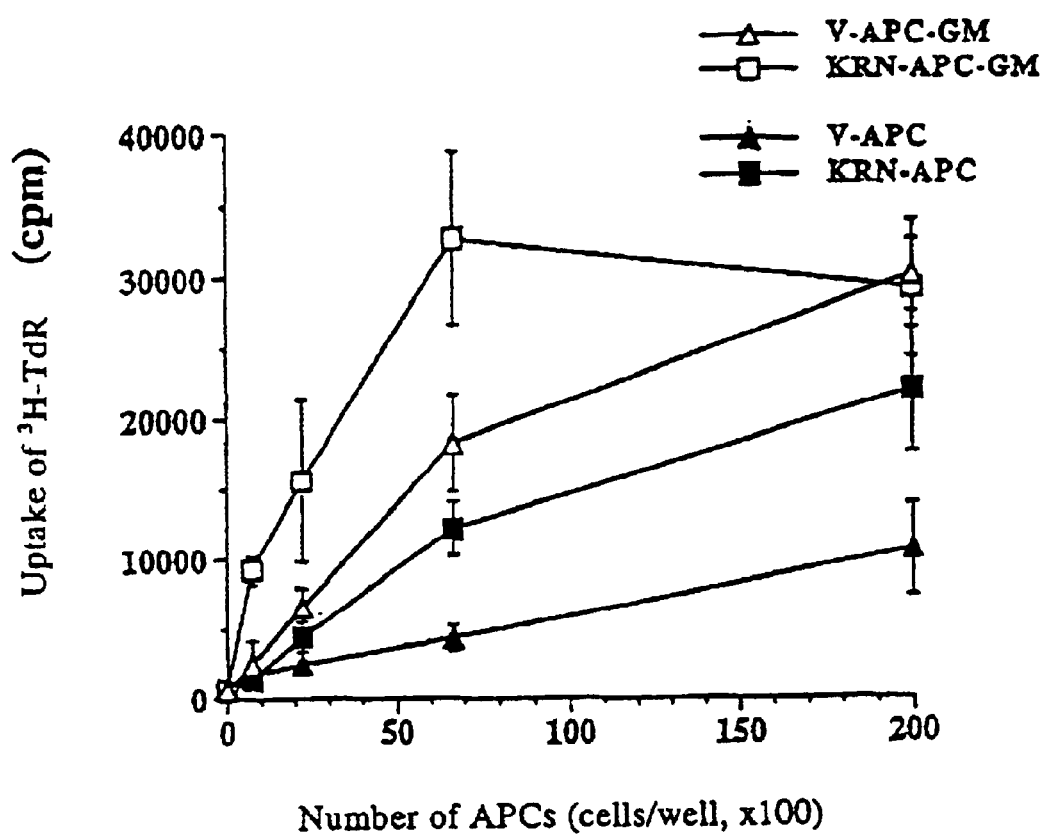
FIG. 10 shows a relationship between the number of APCs given after culturing for 3 days and the amount of $^3$H-TdR taken up into human peripheral blood-derived FcR$^-$ cells.

As shown in FIG. 10, all of the APCs enhanced the allogeneic MLR response in a manner dependent on the number of the APCS, however, KRN-APC and KRN-APC-GM showed a clearly stronger stimulatory effect on the proliferation of responder cells compared to V-APC and V-APC-GM, respectively. Furthermore, it was also found that the effect of KRN-APC-GM was stronger than KRN-APC. It is assumed that the suppressed proliferation of the responder cells by the addition of KRN-APC-GM in an amount of 20000 cells/well is due to the over growth of the responder cells.

Pharmacological Test 10

Effect of KRN7000 on Human Peripheral Blood-derived APC

To study the effect of long-term culture of APC, the following experiment was performed. A monocyte fraction was prepared from human peripheral mononuclear cells by Percol density-gradient centrifugation. The monocyte fraction was cultured in the presence of GM-CSF (50 ng/mL) and IL-4 (100 ng/mL), and simultaneously either a vehicle (V; 0.1% DMSO) or KRN7000 (KRN; 100 ng/mL) was added thereto. After culturing for 7 days, the cells were recovered and washed with the medium 3 times to give V-APC-GM and KRN-APC-GM, respectively, which were provided for use as APCs. As responder cells, human peripheral blood-derived FcR$^-$ cells were used to perform autologous MLR assay.

Figure 11:
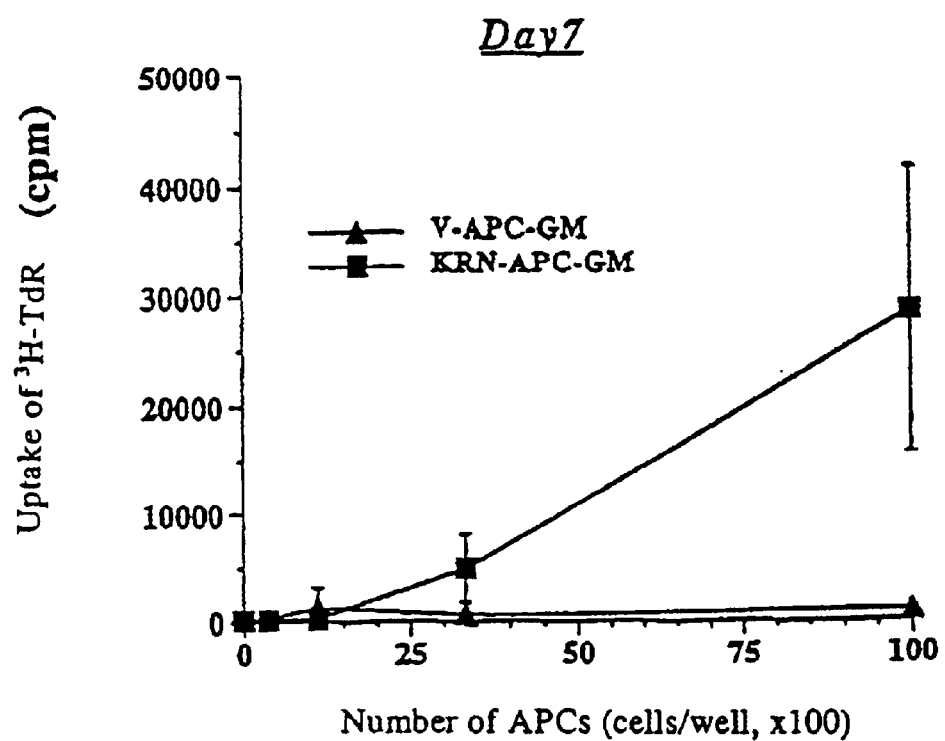
FIG. 11 shows a relationship between the number of APCs given after culturing for 7 days and the amount of $^3$H-TdR taken up into human peripheral blood-derived FcR$^-$ cells.

As shown in FIG. 11, V-APC-GM did not stimulate the proliferation of the responder cells, whereas KRN-APC-GM enhanced the autologous MLR response in a manner dependent on the number of the APCs.

Pharmacological Test 11

Effect of KRN7000 on Human Peripheral Blood-derived APC

To study the effect of long-term culture of APC, the following experiment was performed. A monocyte fraction was prepared from human peripheral mononuclear cells by Percol density-gradient centrifugation. The monocyte fraction was cultured in the presence of GM-CSF (50 ng/mL) and IL-4 (100 ng/mL) with or without monocyte conditioned medium (MCM) prepared by the method of Bender et al (Bender A. et al., 1996, J. Immunol. Method., 196, 121). Simultaneously either a vehicle (V; 0.1% DMSO) or KRN7000 (KRN; 100 ng/mL) was added to the fraction. After culturing for 11 days, the cells were recovered and washed with the medium 3 times to give V-APC-GM (MCM−), KRN-APC-GM (MCM−), V-APC-GM (MCM+) and KRN-APC-GM (MCM+), respectively, which were provided for use as APCs. As responder cells, human peripheral blood-derived FcR$^-$ cells were used to perform autologous MLR assay.

Figure 12:
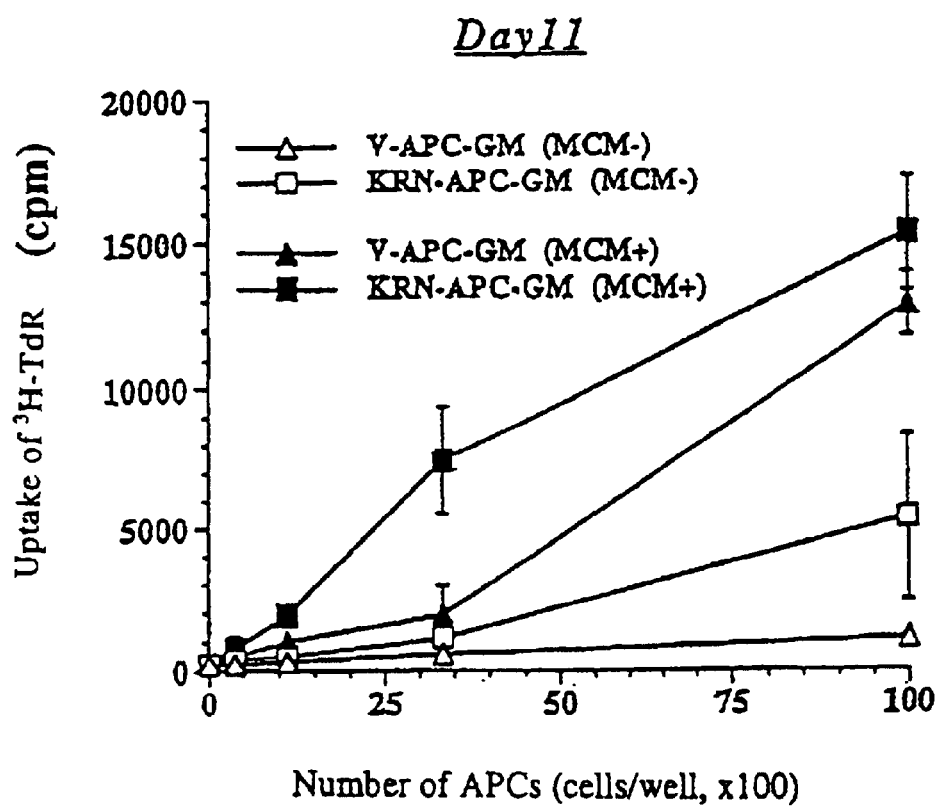
FIG. 12 shows a relationship between the number of APCs given after culturing for 11 days and the amount of $^3$H-TdR taken up into human peripheral blood-derived FcR$^-$ cells.

As shown in FIG. 12, V-APC-GM (MCM−) did not stimulate the proliferation of the responder cells, whereas KRN-APC-GM (MCM−) enhanced the autologous MLR response in a manner dependent on the number of the APCs. Both V-APC-GM (MCM+) and KRN-APC-GM (MCM+) enhanced the autologous MLR response in a manner dependent on the number of the APCs. The effect of KRN-APC-GM (MCM+) was stronger than that of V-APC-GM (MCM+).

From the results of Pharmacological Tests 9, 10 and 11 above, it has been found that KRN7000 can activate the APCs from human peripheral blood by various methods.

Pharmacological Test 12

Effect of KRN7000 on Human Umbilibal Cord Blood-derived APC

A monocyte fraction was prepared from human umbilical cord blood mononuclear cells by Percol density-gradient centrifugation. The monocyte fraction was cultured in the presence of GM-CSF (50 ng/mL) and IL-4 (100 ng/mL), and simultaneously either a vehicle (V; 0.1% DMSO) or KRN7000 (KRN; 100 ng/mL) was added thereto. After culturing for 3 days, the cells were recovered and washed with the medium 3 times to give V-APC-GM and KRN-APC-GM, respectively, which were provided for use as APCs. As response cells, human umbilical cord blood-derived FcR$^-$ cells were used for autologous MLR assay.

Figure 13:
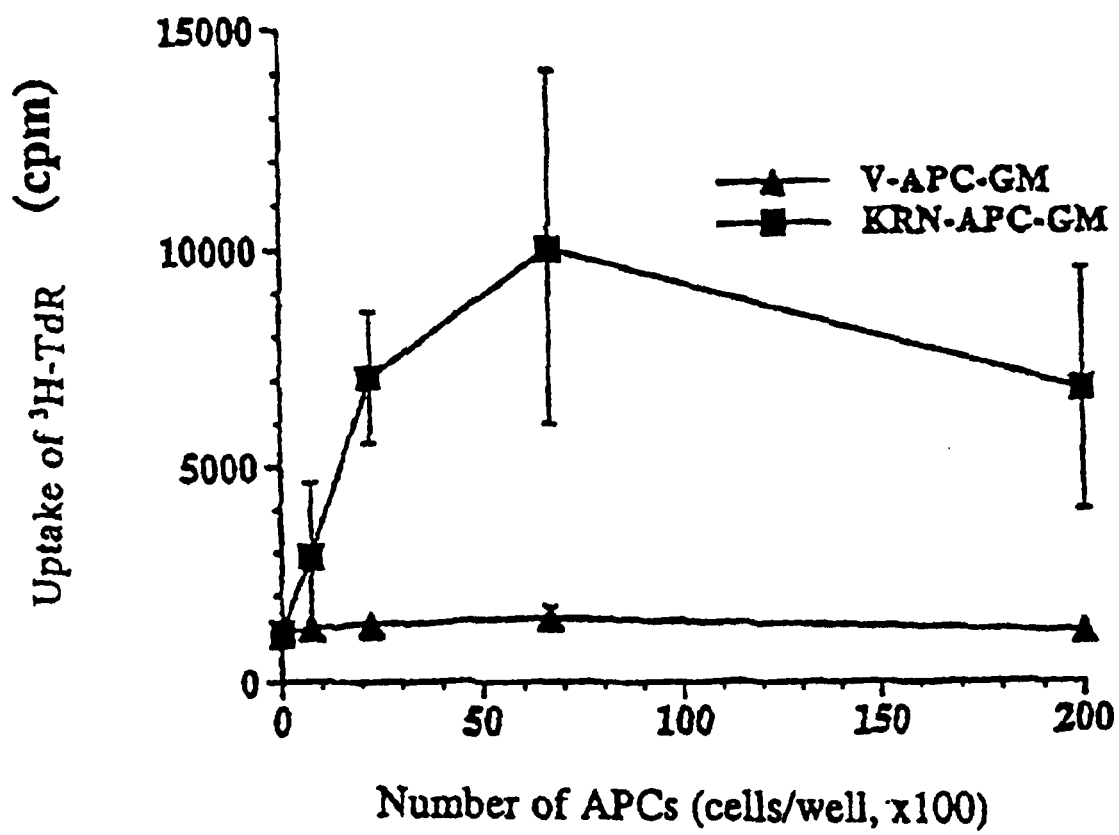
FIG. 13 shows a relationship between the number of APCs given after culturing for 3 days and the amount of $^3$H-TdR taken up into human umbilical cord blood-derived FcR$^-$ cells.

As shown in FIG. 13, V-APC-GM did not stimulate the proliferation of the responder cells, whereas KRN-APC-GM enhanced the autologous MLR response in a manner dependent on the number of the APCS. It is assumed that the suppressed proliferation of the responder cells by the addition of KRN-APC-GM in an amount of 20,000 cells/well is due to the over growth of the responder cells.

This result shows that KRN7000 can activate the APCs derived from human umbilical cord blood by various methods.

Pharmacological Test 13

Effect of α-galactosylceramides on Murine Spleen-derived APC

To demonstrate that the α-galactosylceramide derivatives of the present invention other than KRN7000 also have an APC-activating effect, the following pharmacological test was performed.

The dendritic cell-rich APCs were prepared from murine spleen in the same manner as described in Pharmacological Test 3. Briefly, the APCs were treated with any one of KRN7000 (Compound No.14 of the invention), AGL512

(Compound No.10 of the invention), AGL525 (Compound No.16 of the invention), AGL506 (Compound No.1 of the invention), AGL514 (Compound No.2 of the invention), AGL571 (Compound No.5 of the invention) and a vehicle (DMSO, final concentration: 0.1%) at the final concentration of 100 ng/mL. Each of the APCs thus treated ($1\times10^4$ cells/well) and the responder cells ($2.5\times10^5$ cells/well) were added to wells of a 96-well plate and then subjected to syngeneic MLR assay. After culturing for 2 days, $^3$H-TdR was added to each well (0.5 μCi/well). After 8 hours, the cells were harvested, and the amount of the $^3$H-TdR taken up into the cells was determined using a liquid scintillation counter. The results are shown in FIG. 14.

Figure 14:
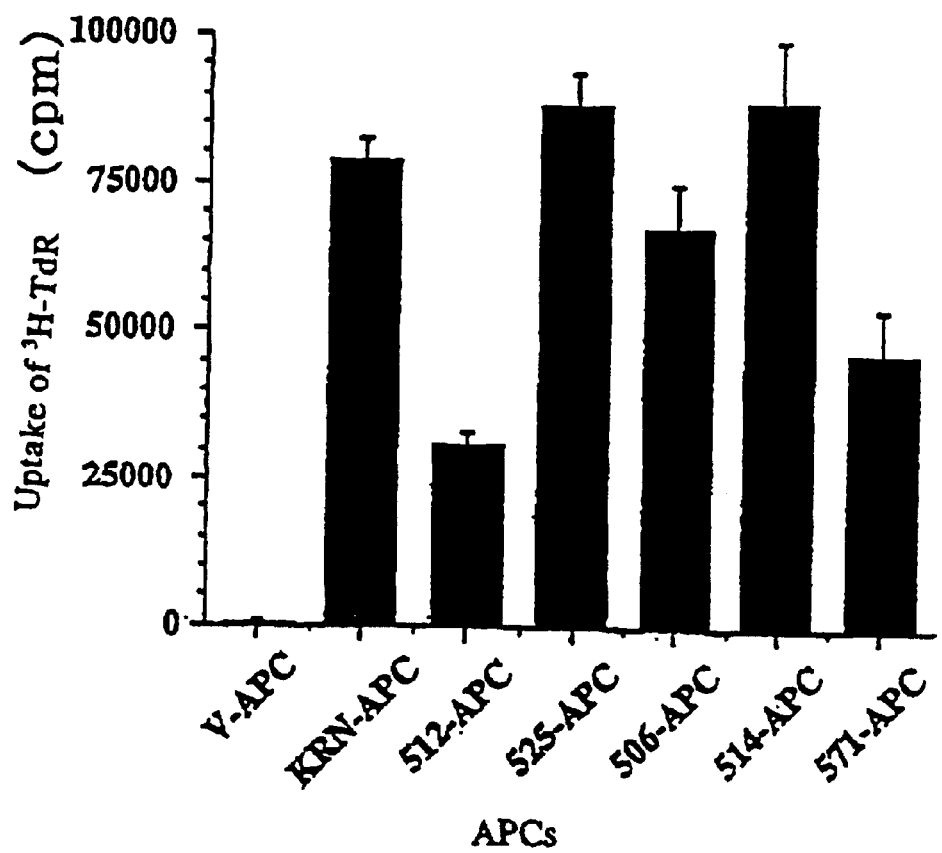
FIG. 14 shows activation effect of murine spleen-derived APCs when they are stimulated by Compounds Nos. 1, 2, 5, 10 and 16 (except KRN7000), termed AGL506, AGL514, AGL571, AGL512 and AGL525, respectively.

In FIG. 14, "V-APC", "KRN-APC", "512-APC", "525-APC", "506-APC", "514-APC" and "571-APV" refer to the APCs pretreated with the vehicle, KRN7000, AGL-512, AGL-525, AGL-506, AGL-514 and AGL-571, respectively.

As shown in FIG. 14, the APCs pretreated with α-galactosylceramide derivatives showed a remarkable syngeneic MLR enhancing effect.

This result shows that the compounds of the present invention (α-galactosylceramides and α-glucosylceramides) other than KRN7000 also have an effect of activating the dendritic cell-rich APCs derived from murine spleen (i.e., an APC function-enhancing effect).

What is claimed is:

1. A method for activating a human antigen-presenting cell, comprising culturing human dendritic cells in vitro with at least one of the glycoside compounds represented by formula (A) or salts thereof and a tumor antigen:

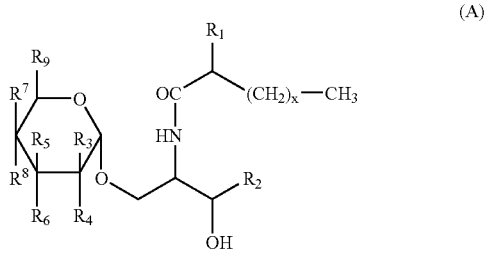

(A)

wherein
$R_1$ is H or OH;
X is an integer of from 7 to 25;
$R_2$ is a substituent defined by any one of the following (a) to (e):
(a) —$CH_2(CH_2)_YCH_3$;
(b) —$CH(OH)(CH_2)_YCH_3$;
(c) —$CH(OH)(CH_2)_YCH(CH_3)_2$;
(d) —$CH=CH(CH_2)_YCH_3$; and
(e) —$CH(OH)(CH_2)_YCH(CH_3)CH_2CH_3$
wherein Y is an integer of from 5 to 17;
$R_3$ is H;
$R_4$ is OH;
$R_5$ is OH;
$R_6$ is H;
one of $R_7$ and $R_8$ is H and the other is OH; and
$R_9$ is H, $CH_3$ or $CH_2OH$.

2. The method of claim 1, wherein the human dendritic cells are obtained by culturing human monocytes in vitro in the presence of GM-CSF and IL-4.

3. The method of claim 2, wherein the human monocyte is prepared from human peripheral blood.

4. The method of claim 2, wherein the human monocyte is prepared from human umbilical cord blood.

5. The method of claim 2, wherein the human monocyte is prepared from a human bone marrow cell.

6. The method of claim 2, wherein the human monocyte is prepared from human epidermis.

7. The method of claim 1 or 2, wherein the glycoside compound is a compound represented by formula (B):

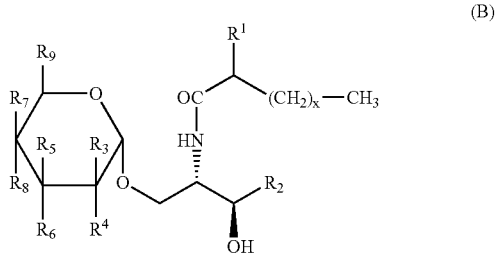

(B)

wherein:
$R_1$ is H or OH;
X is an integer of from 7 to 25;
$R_2$ is a substituent defined by any one of the following (a) to (e):
(a) —$CH_2(CH_2)_YCH_3$;
(b) —$CH(OH)(CH_2)_YCH_3$;
(c) —$CH(OH)(CH_2)_YCH(CH_3)_2$;
(d) —$CH=CH(CH_2)_YCH_3$; and
(e) —$CH(OH)(CH_2)_YCH(CH_3)CH_2CH_3$
wherein Y is an integer of from 5 to 17;
$R_3$ to $R_9$ are substituents defined by any one of the following (i) to (ii):
(i)
$R_3$, $R_6$ and $R_8$ are each H;
$R_4$ is OH;
$R_5$ is OH;
$R_7$ is OH; and
$R_9$ is H, $CH_3$, or $CH_2OH$;
(ii)
$R_3$, $R_6$ and $R_7$ are each H;
$R_4$, $R_5$ and $R_9$ are as defined as in (i); and
$R_8$ is OH.

8. The method of claim 1 or 2, wherein the glycoside compound is a compound represented by formula (B):

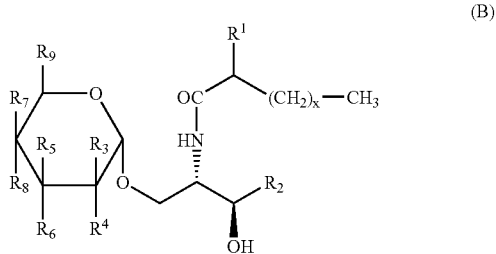

(B)

wherein:
$R_1$ is H or OH;
X is an Integer of from 7 to 25;
$R_2$ is a substituent defined by any one of the following (a) to (e):
(a) —$CH_2(CH_2)_YCH_3$;
(b) —$CH(OH)(CH_2)_YCH_3$;
(c) —$CH(OH)(CH_2)_YCH(CH_3)_2$;
(d) —$CH=CH(CH_2)_YCH_3$; and
(e) —$CH(OH)(CH_2)_YCH(CH_3)CH_2CH_3$
where Y is an integer of from 5 to 17;

$R_3$, $R_6$, and $R_8$ are each H;

$R_4$, $R_5$, and $R_7$ are each OH; and $R_9$ is $CH_2OH$.

9. The method of claim 1 or 2, wherein the glycoside compound is a compound represented by formula (B):

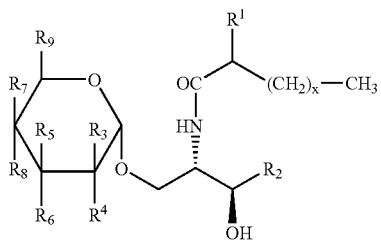

(B)

wherein $R_1$ is H or OH;

X is an integer of from 7 to 25;

$R_2$ is a substituent defined by any one of the following:
 (b) —$CH(OH)(CH_2)_yCH_3$;
 (c) —$CH(OH)(CH_2)_yCH(CH_3)_2$; and
 (e) —$CH(OH)(CH_2)_yCH(CH_3)CH_2CH_3$; wherein Y is an integer of from 5 to 17; and $R_3$, $R_6$ and $R_8$ are each H;

$R_4$, $R_5$ and $R_7$ are each OH; and $R_9$ is $CH_2OH$.

10. The method of claim 1 or 2, wherein the glycoside compound is a compound represented by formula (B):

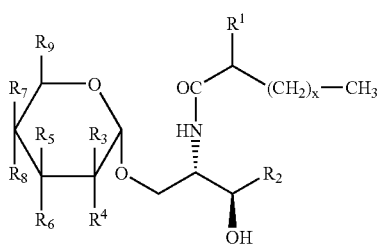

(B)

wherein

X is an integer of from 7 to 25;

$R_1$ is H;

$R_2$ is —$CH(OH)(CH_2)_yCH_3$ where Y is an integer of from 5 to 17;

$R_3$, $R_6$ and $R_8$ are each H;

$R_4$, $R_5$ and $R_7$ are each OH; and $R_9$ is $CH_2OH$.

11. The method of claim 1 or 2, wherein the glycoside compound is a compound represented by formula (B):

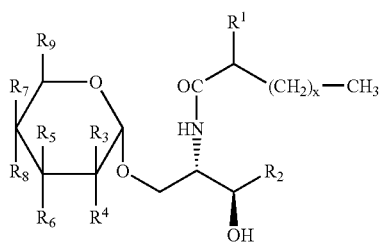

(B)

wherein

X is an integer of from 7 to 25;

$R_1$ is H;

$R_2$ is —$CH(OH)(CH_2)_yCH_3$ where Y is an integer of from 5 to 17 and where the OH group is of R configuration; and $R_3$, $R_6$ and $R_8$ are each H;

$R_4$, $R_5$ and $R_7$ are each OH; and $R_9$ is $CH_2OH$.

12. The method of claim 1 or 2, wherein the glycoside compound is a compound represented by formula (B):

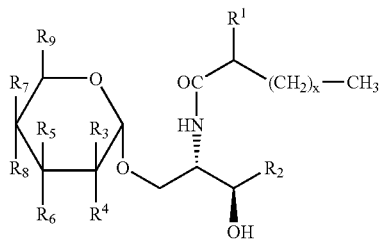

(B)

wherein

X is from 21 to 25 and Y is an integer of from 11 to 15;

$R_1$ is H;

$R_2$ is —$CH(OH)(CH_2)_yCH_3$ where Y is an integer of from 5 to 17 and where the OH group is of R configuration; and $R_3$, $R_6$ and $R_8$ are each H;

$R_4$, $R_5$ and $R_7$ are each OH; and $R_9$ is $CH_2OH$.

13. The method of claim 1 or 2, wherein the glycoside compound is selected from the group consisting of:
 (2S, 3S, 4R)-1-(α-D-galactopyranosyloxy)-2-hexacosanoylamino-3,4-octadecanediol;
 (2S, 3R)-1-(α-D-galactopyranosyloxy)-2-[(R)-2-hydroxytetracosanoylamino]-3-octadecanol;
 (2S, 3R)-1-(α-D-galactopyranosyloxy)-2-tetracosanoylamino-3-octadecanol;
 (2S, 3R)-1-(6'-deoxy-α-D-galactopyranosyloxy)-2-tetracosanoylamino-3-octadecanediol;
 (2S, 3S, 4R)-1-(α-D-galactopyranosyloxy)-2-[(R)-2-hydroxytetracosanoylamino]-3,4-octadecanediol; and
 (2S, 3S, 4R)-1-(α-D-galactopyranosyloxy)-2-tetracosanoylamino-3,4-octadecanediol.

14. The method for activating human antigen-presenting cell of any one of claims 1–6, wherein the tumor antigen is associated with melanoma.

15. The method for activating human antigen-presenting cell of claim 7, wherein the tumor antigen is associated with melanoma.

16. The method for activating human antigen-presenting cell of claim 8, wherein the tumor antigen is associated with melanoma.

17. The method for activating human antigen-presenting cell of claim 9, wherein the tumor antigen is associated with melanoma.

18. The method for activating human antigen-presenting cell of claim 10, wherein the tumor antigen is associated with melanoma.

19. The method for activating human antigen-presenting cell of claim 11, wherein the tumor antigen is associated with melanoma.

20. The method for activating human antigen-presenting cell of claim 12, wherein the tumor antigen is associated with melanoma.

21. The method for activating human antigen-presenting cell of claim 13, wherein the tumor antigen is associated with melanoma.

* * * * *